United States Patent
Vaidya

(12) 
(10) Patent No.: US 8,814,916 B2
(45) Date of Patent: *Aug. 26, 2014

(54) METHOD AND APPARATUS FOR MINIMALLY INVASIVE SUBCUTANEOUS TREATMENT OF HUMERUS FRACTURES

(76) Inventor: Rahul Vaidya, Tecumseh (CA)

(*) Notice: Subject to any disclaimer, the term of this patent is extended or adjusted under 35 U.S.C. 154(b) by 391 days.

This patent is subject to a terminal disclaimer.

(21) Appl. No.: 13/200,067

(22) Filed: Sep. 19, 2011

(65) Prior Publication Data

US 2012/0010665 A1 Jan. 12, 2012

Related U.S. Application Data

(63) Continuation-in-part of application No. 12/592,476, filed on Nov. 27, 2009, now Pat. No. 8,398,686.

(51) Int. Cl.
*A61B 17/88* (2006.01)
*A61F 2/46* (2006.01)
*A61B 17/80* (2006.01)

(52) U.S. Cl.
CPC ............ *A61B 17/80* (2013.01); *A61B 17/8061* (2013.01); *A61B 17/8866* (2013.01)

USPC ......................................... 606/281; 606/86 R

(58) Field of Classification Search
USPC ....... 606/86 R, 105, 280, 281, 283, 284, 291, 606/86 B; 600/53, 54, 57, 59
See application file for complete search history.

(56) References Cited

U.S. PATENT DOCUMENTS 5,364,396 A * 11/1994 Robinson et al. ............... 606/53
5,709,686 A * 1/1998 Talos et al. ................... 606/281
7,524,323 B2 * 4/2009 Malandain .................... 606/246

* cited by examiner

*Primary Examiner* — Anu Ramana
(74) *Attorney, Agent, or Firm* — David W. Schumaker

(57) ABSTRACT

The instant invention is a novel method and construct for temporary or definitive minimally invasive treatment of a broken humerus. The method includes the steps of tunneling an elongated plate subcutaneously in the subcutaneous fat layer substantially parallel to the fractured humerus; and attaching the ends of the elongated plate to the fractured humerus. The elongated plate remains disposed in the subcutaneous fat layer and away from, but parallel to the humerus once attached to the humerus.

19 Claims, 24 Drawing Sheets

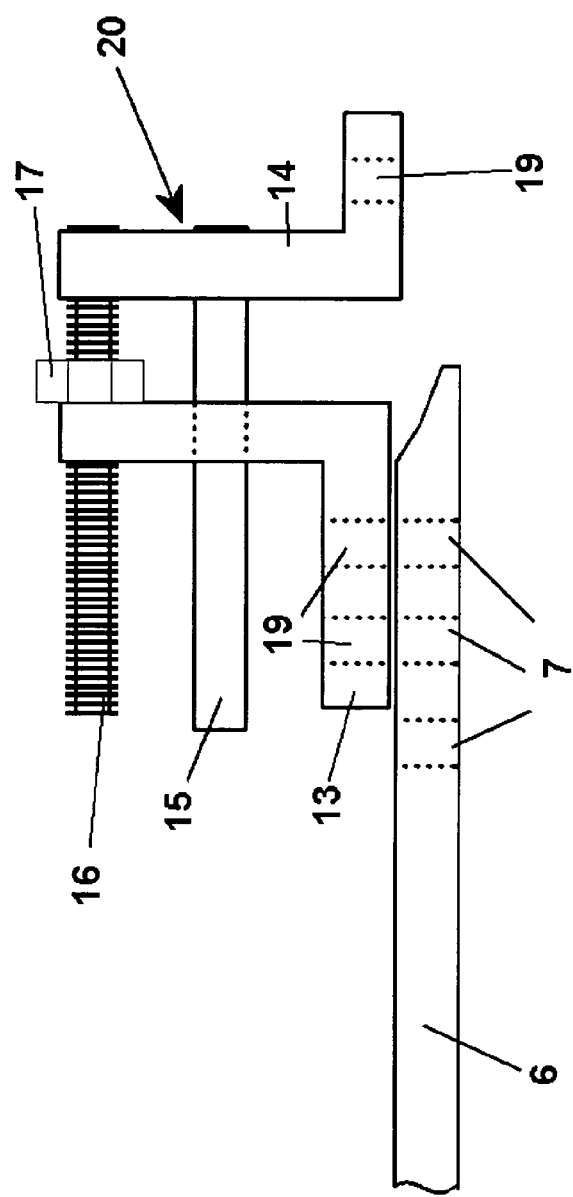
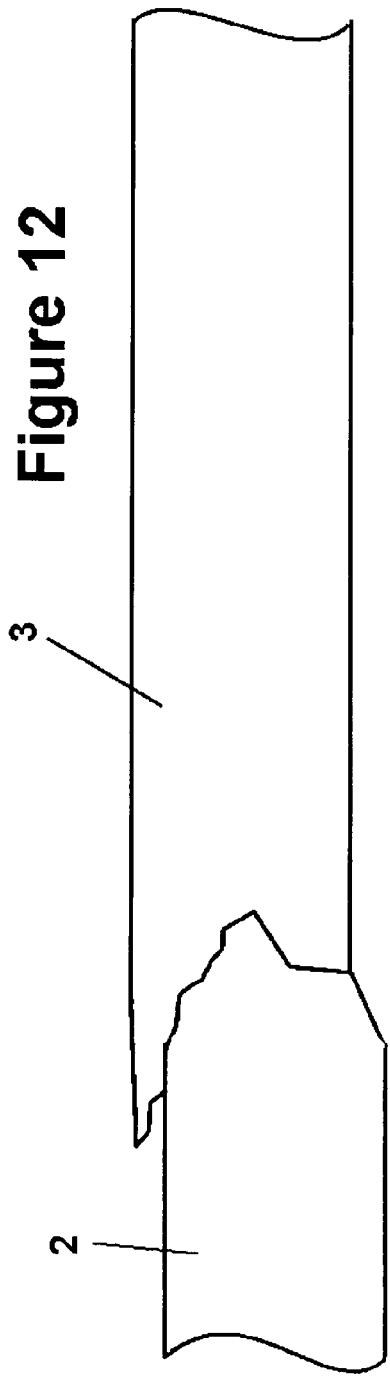
Figure 12

METHOD AND APPARATUS FOR MINIMALLY INVASIVE SUBCUTANEOUS TREATMENT OF HUMERUS FRACTURES

RELATED APPLICATIONS

The present application is a continuation-in-part (CIP) of and claims the benefit of the earlier filing date of U.S. patent application Ser. No. 12/592,476 filed Nov. 27, 2009, now U.S. Pat. No. 8,398,686 titled "Method and Apparatus for Minimally Invasive Subcutaneous Treatment of Long Bone Fractures", published as U.S. Patent Application Publication number 2011/0130794.

FIELD OF THE INVENTION

The present invention relates to methods of temporary and/or permanent fixation of humerus fractures. More specifically the invention relates to minimally invasive subcutaneous treatment of fractures of the humerus. Most specifically the instant invention offers a treatment method and device that is useful for minimally invasive internal fixation of the fractured humerus with no external components and therefore reduced chance for infection. This method and device are highly suitable for battlefield injuries, use in children, and use in third world countries where more extensive treatment may not be available.

BACKGROUND OF THE INVENTION

There are presently two basic techniques for safe transportation of a wounded soldier with a long bone fracture: 1) transportation casts and 2) temporary external fixation. Both of these methods are presently accepted for initial treatment of a patient who will be evacuated out of theater. Precise indications for external fixator use versus casting have not been established.

In general, good indications for external fixator use include when the soft tissues need to be evaluated while en route, such as with a vascular injury; when other injuries make use of casting impractical, such as with a femur fracture and abdominal injury; or when the patients have extensive burns. Advantages of external fixation are that it allows for soft tissue access, can be used for polytrauma patients, and has a minimal physiologic impact on the patient. Disadvantages are the potential for pin site sepsis or colonization and less soft tissue support than casts.

Advantages of transportation casts are that they preserve the maximum number of options for the receiving surgeon; the soft tissues are well supported, and the casts are relatively low tech. Disadvantages are that casts cover soft tissues, may not be suitable for polytrauma patients, and are more labor-intensive than external fixators.

Though standard in civilian trauma centers, intramedullary nailing of major long bone fractures is contraindicated in combat zone hospitals because of a variety of logistical and physiologic constraints. This method may be used once a patient reaches an echelon above corps (EAC) or other site where more definitive care can be provided.

Therefore, although both transportation casts and external fixators are equally acceptable methods for the initial management of long bone fractures, each has its disadvantages. Additionally, current methods of internal fixation are contraindicated, especially considering the extensive length and depth of incision required to place the fixation plate adjacent to the fractured bone. Thus, there is a need in the art for a method and apparatus for the safe transportation of a wounded soldier with a long bone fracture which allows for access to the soft tissues as needed, and yet reduces the chances of infection, sepsis or colonization.

SUMMARY OF THE INVENTION

A surgical method for minimally invasive subcutaneous treatment of humerus fractures. The method may including the step of tunneling an elongated plate subcutaneously and supramuscularly in the subcutaneous fat layer substantially parallel to the fractured humerus. The method may further include the step of attaching the ends of the elongated plate to the fractured humerus, wherein the elongated plate remains disposed in the subcutaneous fat layer and away from, but substantially parallel to the humerus once attached to the humerus.

The tunneling step may include creating one or more incisions in the skin through which the elongated plate can be inserted and the one or more incisions in the skin may be created on the lateral part of the brachium. The step of attaching the ends of the elongated plate to the fractured humerus may include inserting attachment screws through holes in the ends of the elongated plate and into the humerus. The holes in the elongated plate may be threaded and the attachment screws may have threaded heads which allow the attachment screws to lock into the threaded holes of the elongated plate.

The step of attaching the ends of the elongated plate to the fractured humerus may further include the step of inserting the attachment screws through holes in a an angled end of the elongated plate into the lateral epicondyle region of the distal end of the humerus. The step of attaching the ends of the elongated plate to the fractured humerus may further include the step of inserting a threaded rod into the proximal end of the humerus, which is used to hold steady, distract and align the proximal end of the humerus before the step of inserting attachment screws through holes in the ends of the elongated plate and into the humerus.

The step of attaching the ends of the elongated plate to the fractured humerus may further include the step of distracting and aligning the fractured humerus. The step of distracting and aligning the fractured humerus may include inserting a threaded rod into the proximal end of the humerus and manually distracting and aligning the fractured humerus.

The step of distracting and aligning the fractured humerus may include using a distraction device. The step of using a distraction device may include the step of attaching the distraction device to the holes in the proximal end of the elongated plate and also attaching the distraction device to the proximal end of the humerus. The distraction device may have two brackets, where the first of the brackets is attached to the holes in the proximal end of the elongated plate and the second of the brackets is attached to the proximal end of the humerus. The distraction device may further include an expansion device which is attached to both brackets and when used causes the brackets to expand away from each other thereby providing for distraction of the humerus. The expansion device may include a threaded rod and a nut which is threaded onto the threaded rod, wherein the nut pushes against one of the brackets causing the brackets to expand away from each other thereby providing for distraction of the humerus.

The step of attaching the ends of the elongated plate to the fractured humerus may further include the step of inserting an attachment screw through a hole in aproximal end of the elongated plate into the proximal end of the humerus once the step of distracting and aligning the fractured humerus is completed. The step of attaching the ends of the elongated plate to the fractured humerus may further include the step of removing the distraction device after the step of inserting an attachment screw through a hole in the proximal end of the elongated plate into the proximal end of the humerus.

The step of attaching the ends of the elongated plate to the fractured humerus may further include the step of inserting one or more additional attachment screws through the remaining holes in the proximal end of the elongated plate into the proximal end of the humerus. The elongated plate and the attachment screws may be formed from titanium, stainless steel or a bio-compatible polymer material.

BRIEF DESCRIPTION OF THE DRAWINGS

FIG. 12 shows how the distraction device is aligned with plate for temporary

DETAILED DESCRIPTION OF THE INVENTION

Figure 1:
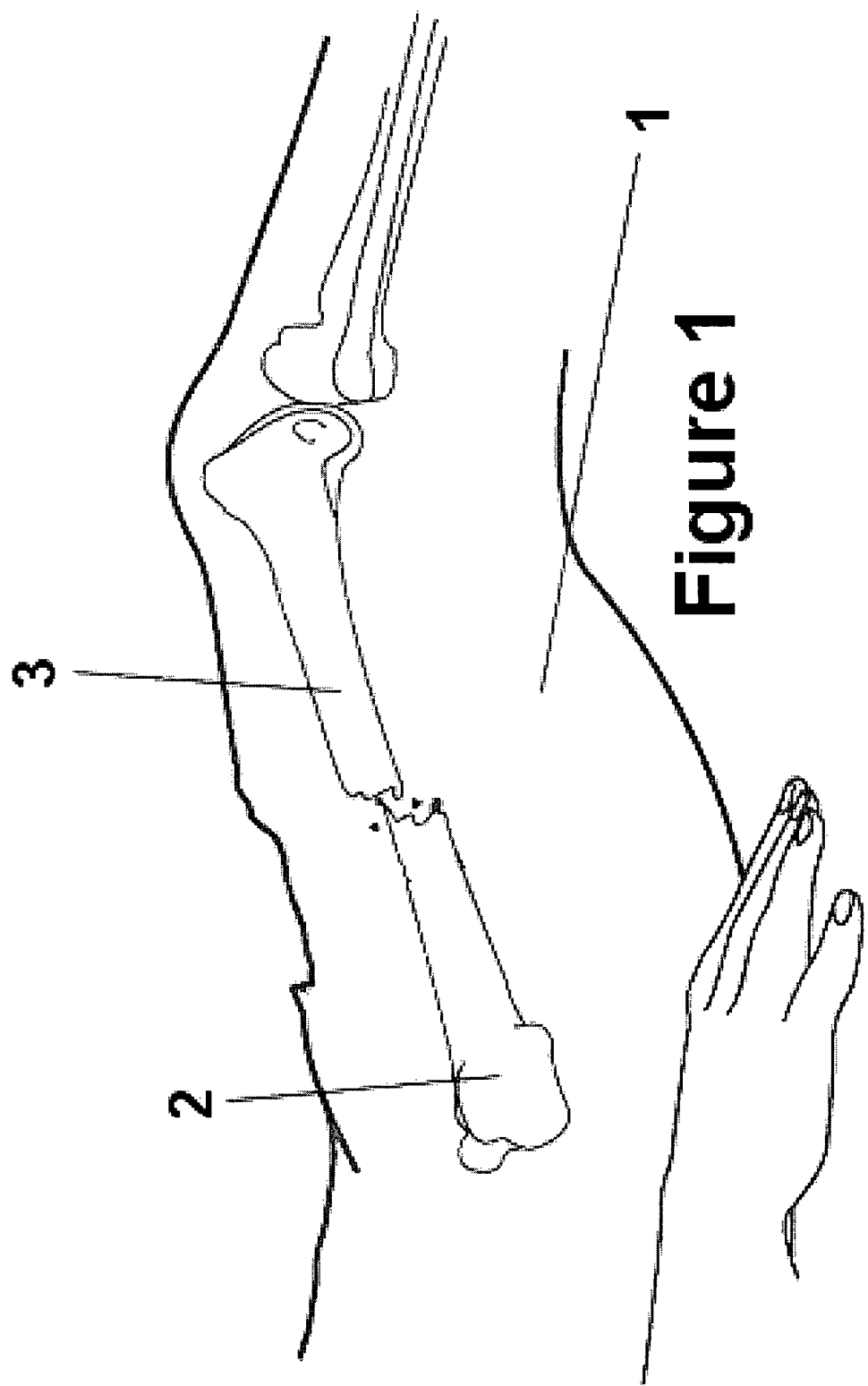
FIG. 1 is a depiction of a thigh having a broken femur.
Figure 2:
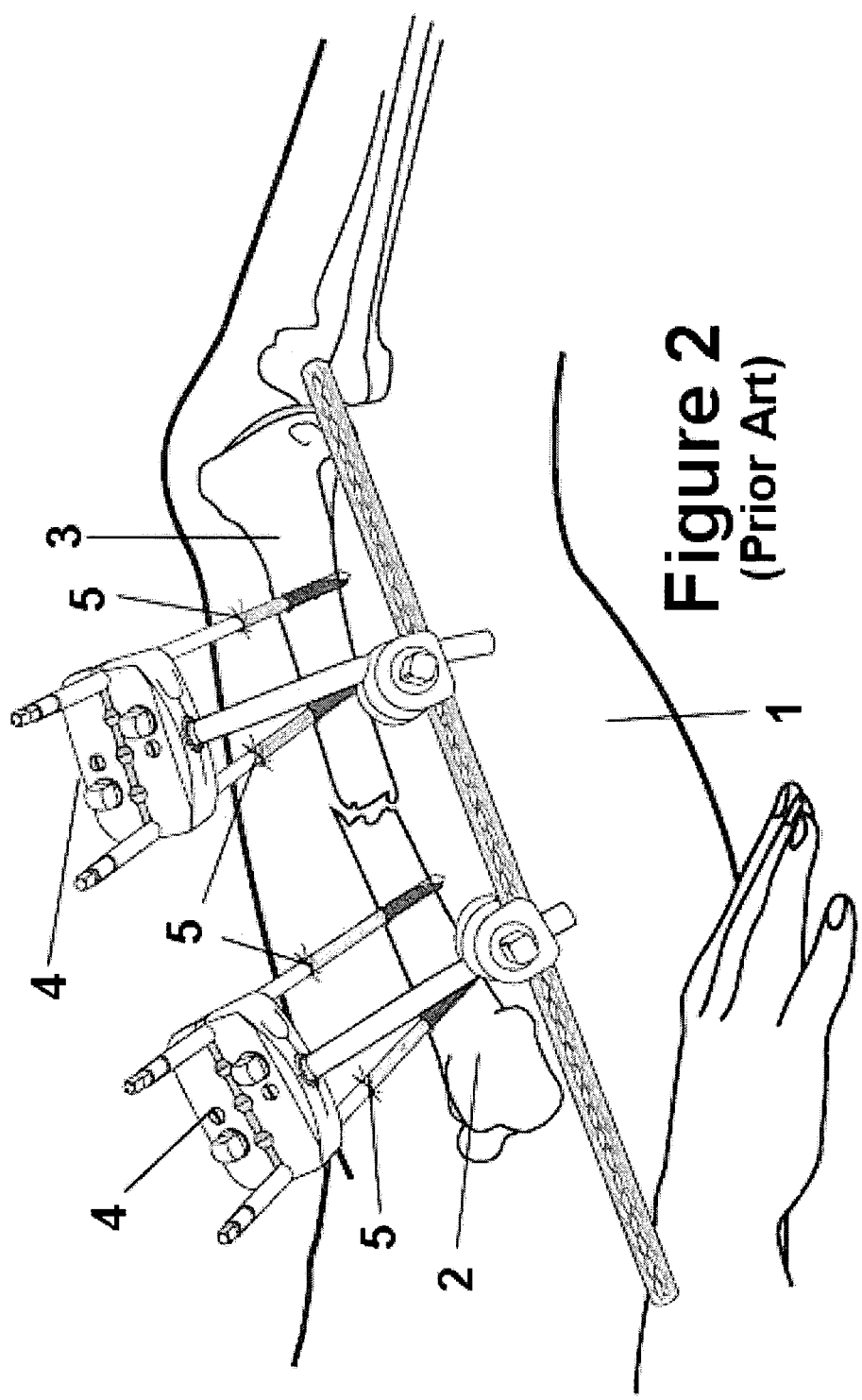
FIG. 2 depicts a prior art external fixation technique showing how the mechanisms of the external fixator are attached by pins to the broken portions of the femur.

The instant invention is a novel method and construct for temporary or definitive minimally invasive treatment of broken long bones such as a femur or humerus. FIG. 1 is a depiction of a thigh 1, having a femur which is broken into two pieces 2 and 3. One aspect of the present invention is an internal fixator for the femur or humerus which sits subcutaneously. The fixator is a plate which is inserted under the skin above the fascia in the subcutaneous space. Its advantage is for transport of military wounded from the field to the definitive care facility. As noted above, currently patients/soldiers are transferred with an external fixator which has pins screwed into the bone connected to bars outside of the skin. FIG. 2 depicts this prior art fixation technique showing how the mechanisms 4 of the external fixator are attached by pins to the broken portions of the femur 2, 3 via holes in the skin 5. The external fixators are cumbersome and can lead to infection. The external fixators need to be replaced by rods or plates at the definitive care facility. If an external fixator is used on a patient for longer than 7 to 10 days there is a risk for pin site infection if it is later decided to nail the femur or humerus. Also because the pins extend from the bone to outside the skin there is always a risk for pin site infection.

With the inventive device and method, definitive surgery can be performed without the risk of infection as the device is under the skin. The device is easy to apply and, because the hardware is totally subcutaneous, it is not unwieldy for the patient or for the transporting team. Medical personnel can safely wait until the soldier is safe for further surgery without the risk of infection.

While the inventive device and method can be used for battlefield trauma of long bones, the treatment can also be used for children between 3 to 12 years of age. The inventive internal fixator can be definitive treatment but should be removed after 8 weeks to 3 months. In this context, the present invention would replace the use of flexible ender nails. The inventive device is much stiffer than flexible ender nails and would not need any other immobilization.

Further, in civilian treatment the present method and device may be used to temporize polytrauma patients as a damage control measure and may later be replaced by conventional internal fixation. The present method and device may be used as definitive care in certain situations when further surgery is not possible. The present method and device would be exceptionally useful in peripheral centers when used to transfer patients after early treatment to a definitive care facility.

Also the inventor notes that the present method and device could be used as definitive fixation in third-world areas where a C-arm is not available as it is easy to apply. Of course, it would still need to be removed after 3 months in adults.

Figure 3:
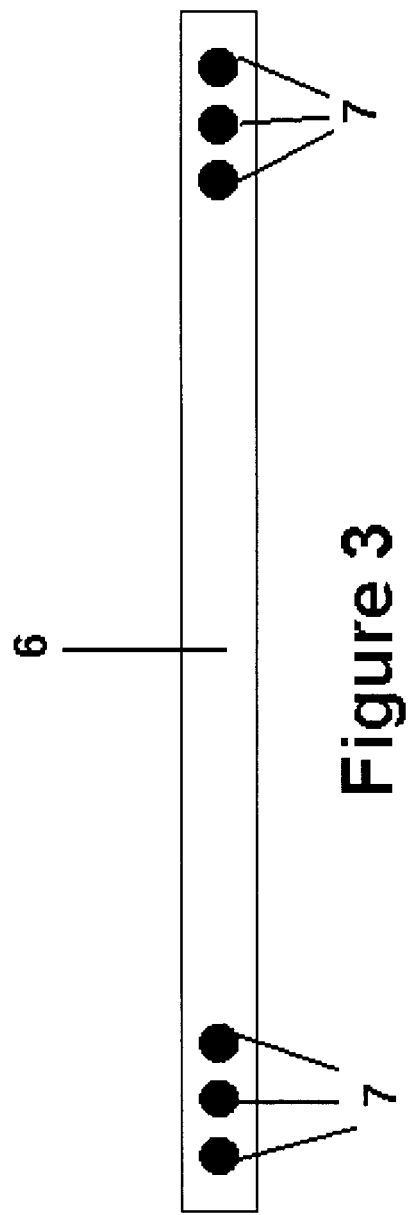
FIG. 3 is a schematic depiction of an elongated plate useful in the present invention.

Turning now to a detailed description of the present method and device, FIG. 3 is a schematic depiction of an elongated plate 6 useful in the present invention. The plate 6 has at least two, and preferably three or more hole 7 in each end thereof. The holes 7 accommodate attachment means to attach the plate to the femur or humerus. The holes 7 may be threaded as in locking plate technology. The holes 7 may also be non-threaded and the attachment means may include screws and nuts which can lock the plate near the end of the screws remote from the bone. It should be noted that elongated plate is based on locking plate technology but since it has significantly fewer holes, the device will cost less to produce. Also, the plate 6 is preferably smooth and any screw holes 7 in the plate that are not filled with attachment screws 10 should be filled with a sham screw to avoid soft tissue growing into the holes 7 as this will make the plate 6 difficult to remove.

Figure 4:
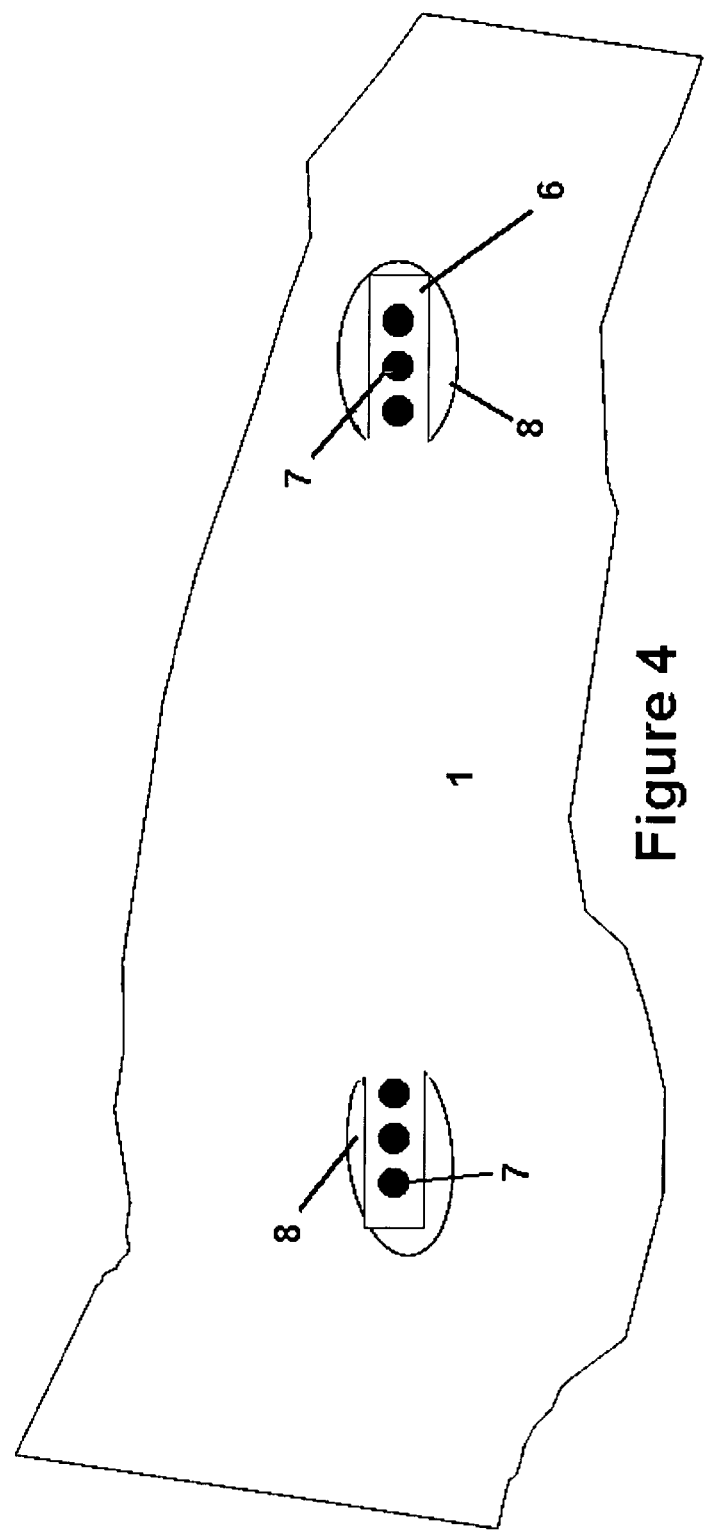
FIG. 4 is a schematic depiction of the manner in which the elongated plate may be placed subcutaneously in the thigh.
Figure 5:
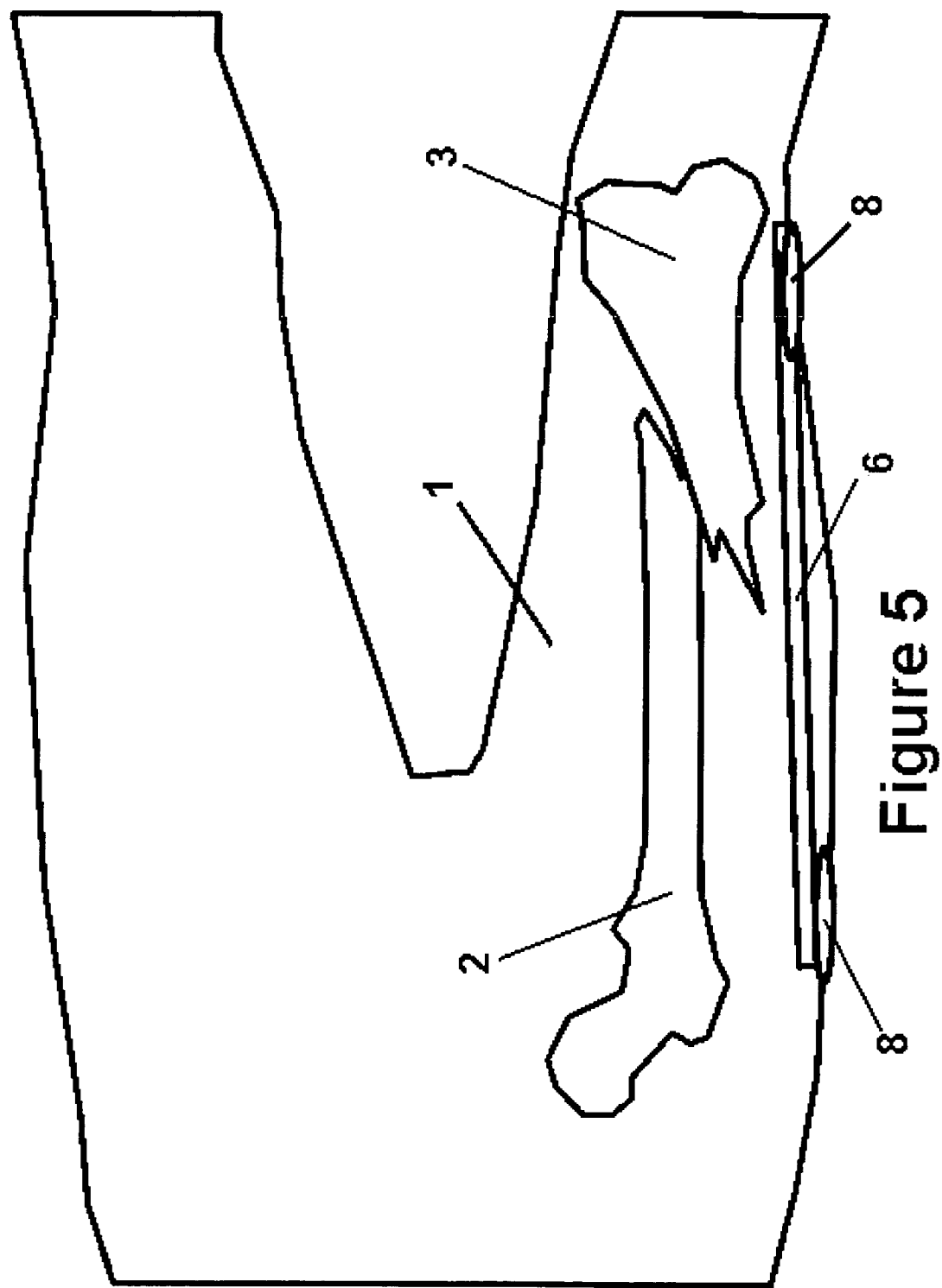
FIG. 5 is a schematic depiction of an alternative view of the manner in which the elongated plate is tunneled subcutaneously inside the thigh parallel to the broken femur between two incisions.

FIG. 4 is a schematic depiction of the manner in which the elongated plate 6 may be placed subcutaneously in the thigh 1. The plate 6 may be placed into the subcutaneous fat layer through two incisions 8 in the skin. One incision is near the proximal end of the bone and one is near the distal end of the bone. The incisions 8 may be approximately 2 inches or less on each end and may preferably be placed in the lateral anterior area of the thigh 1 when the bone being fixated 2,3 is a femur. Of course, the plate 6 may come in many different sizes to accommodate different bone sizes. This placement of the elongated plate 6 just under the skin prevents disruption of the muscle tissue and since there is no dissection, there is little chance for infection. FIG. 5 is a schematic depiction of an alternative view of the manner in which the elongated plate is tunneled subcutaneously inside the thigh 1 parallel to the broken femur 2,3 between the two incisions 8.

Figure 6:
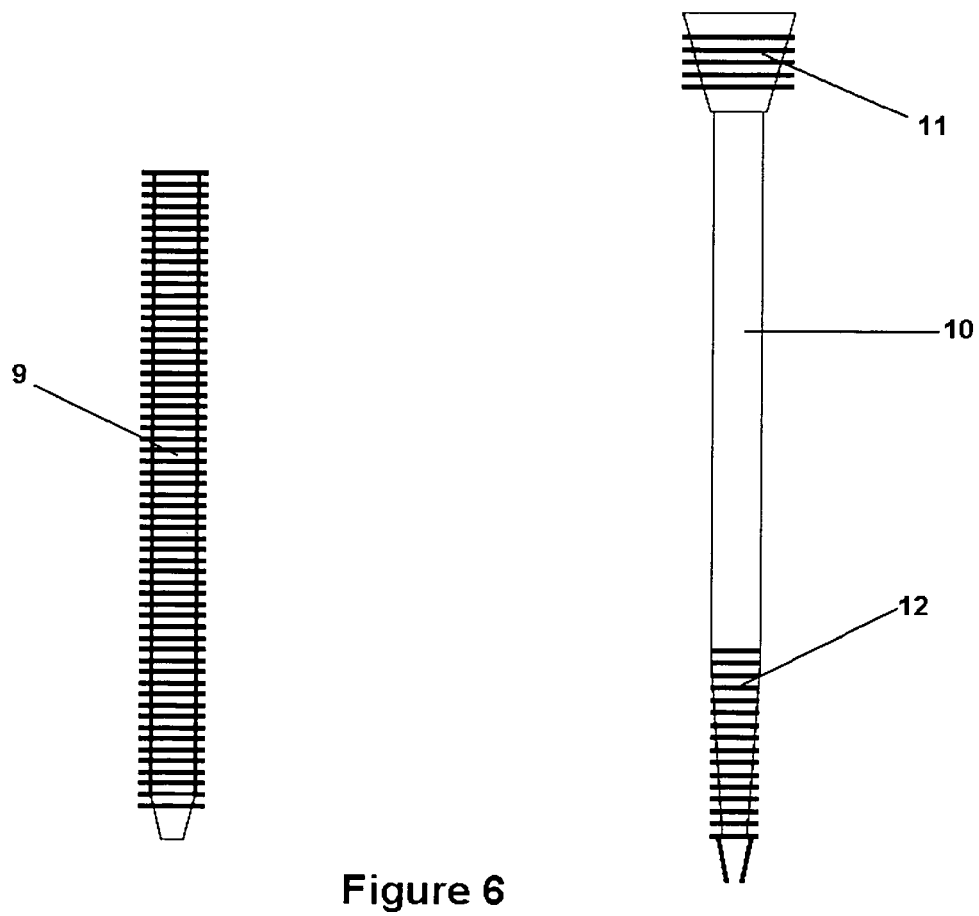
FIG. 6 shows attachment means which may be used in the inventive method and device.

FIG. 6 shows attachment means which may be used in the inventive method and device. Threaded rods 9 may be used to hold the broken bone sections steady as screws 10 are used to attach the device to the bone. Attachment screw 10 preferably has a threaded head 11 to cooperate with the threading in the holes of the elongated plate. Further, the shaft of screw 10 preferably has thread 12 only on the end thereof that will be inserted into the bone. Attachment screws 10 may be cortical screws, such as uni-cortical or bi-cortical screws. Alternatively, threaded rod 9 may be used to steady and attach the plate to the bone using nuts or the like to anchor the plate to the rod in the subcutaneous position, with or without a separate threaded rod 9 for manual manipulation of the bone.

Figure 7:
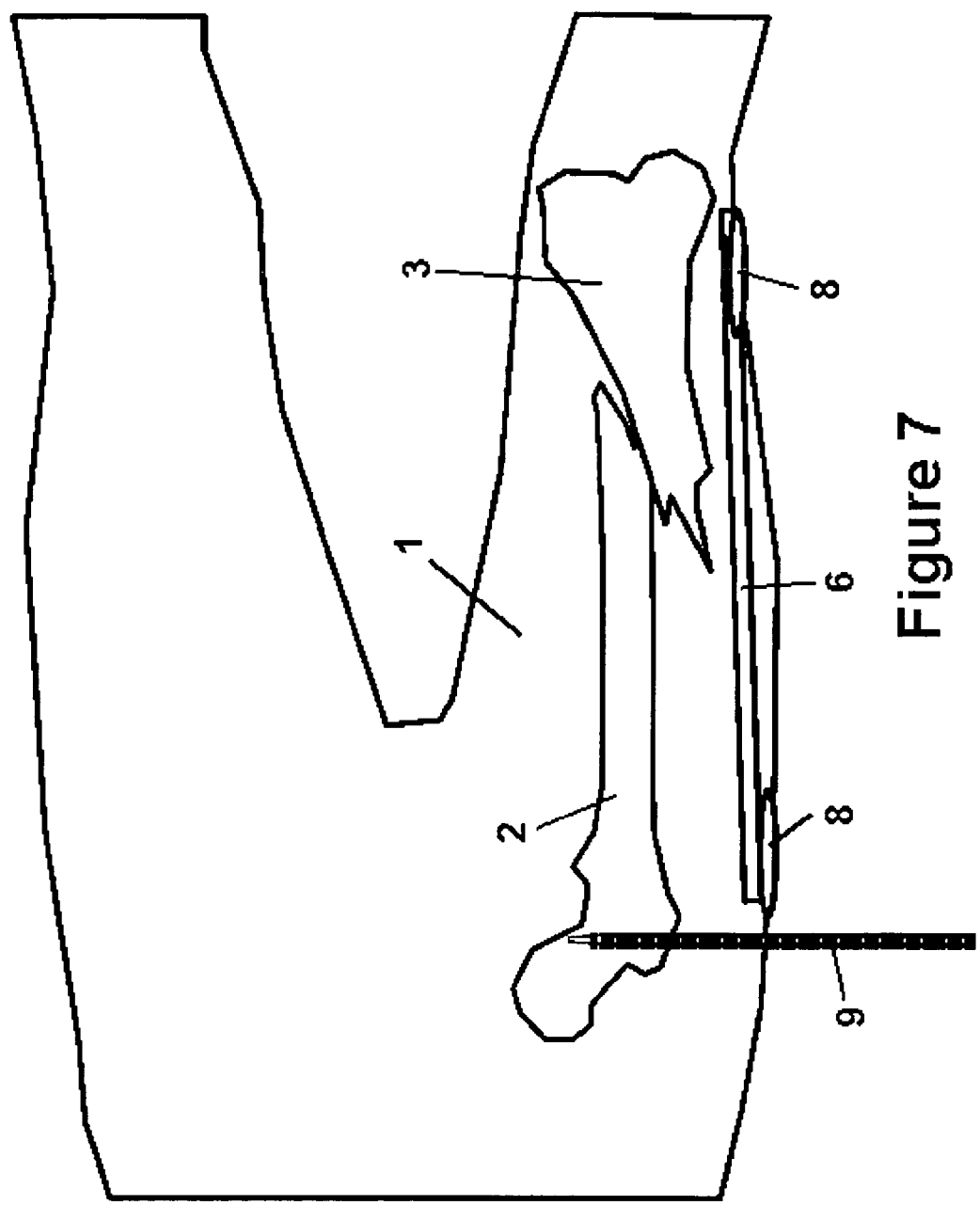
FIG. 7, depicts how a threaded rod 9 may be placed into one end of the bone after the plate has been placed into the thigh.
Figure 8:
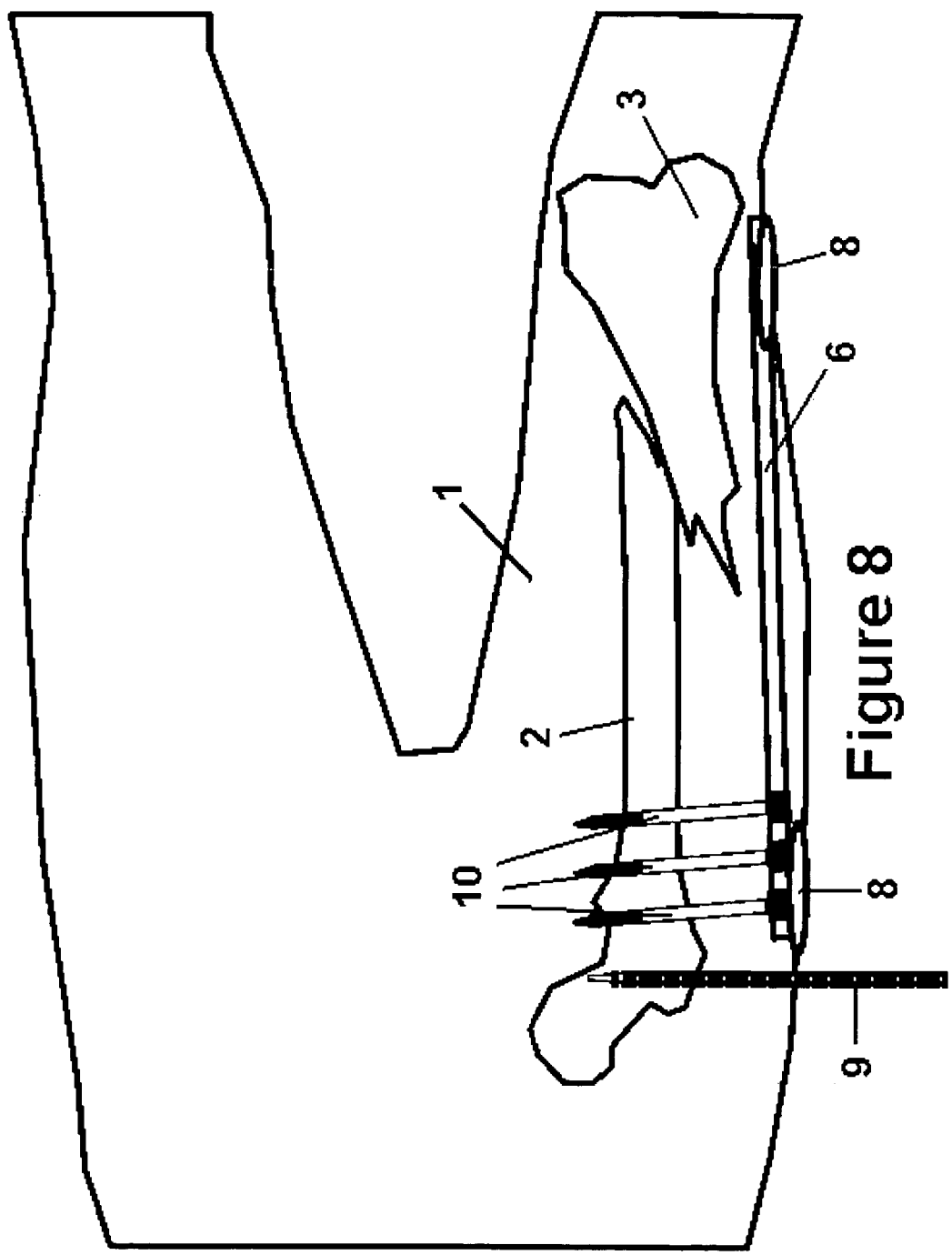
FIG. 8, attachment means 10 are inserted through the incision 8, through the holes in the elongated plate 6 and into the bone 2.
Figure 9:
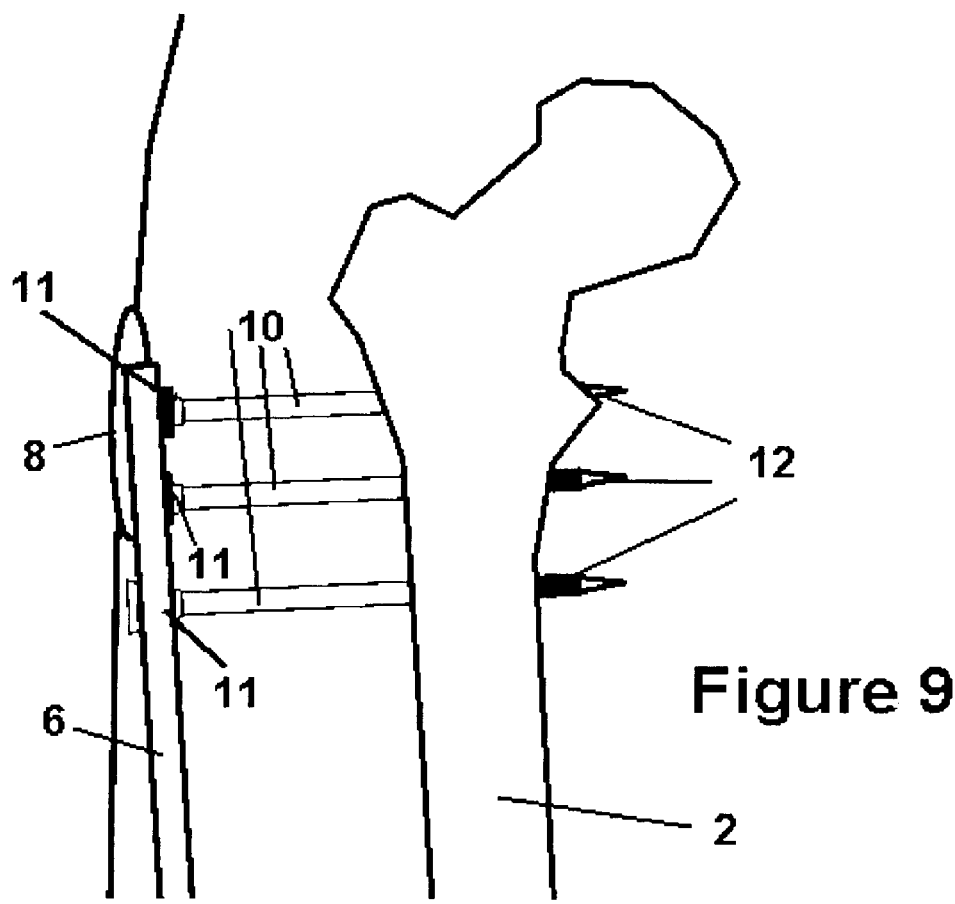
FIG. 9 depicts the results of insertion of three of attachment screws through the plate into the bone.

As shown in FIG. 7, once the plate 6 has been placed into the thigh, a threaded rod 9 may be placed into one end of the bone 2. Preferably the rod 9 is placed into the proximal end of the bone. This threaded rod may be used to hold the bone in place as the plate 6 is attached to the bone. Next, as shown in FIG. 8, attachment means 10 are inserted through the incision 8, through the holes in the elongated plate 6 and into the bone 2. As stated above, the plate 6 may have 2 or more holes in each end, preferably 3 or more. FIG. 9 depicts the results of insertion of three attachment screws 10 through the plate 6 into the bone. Also shown is the manner in which the threaded heads of the screws 10 lock into the threaded holes of the plate 6 and the manner in which the shaft of the screw 10 preferably only has thread 12 only on the portion thereof which is inserted into the bone 2. As can be seen the threaded rod 9 is removed from the proximal end of the bone 2 once the attachment screws 10 are in place.

Figure 10:
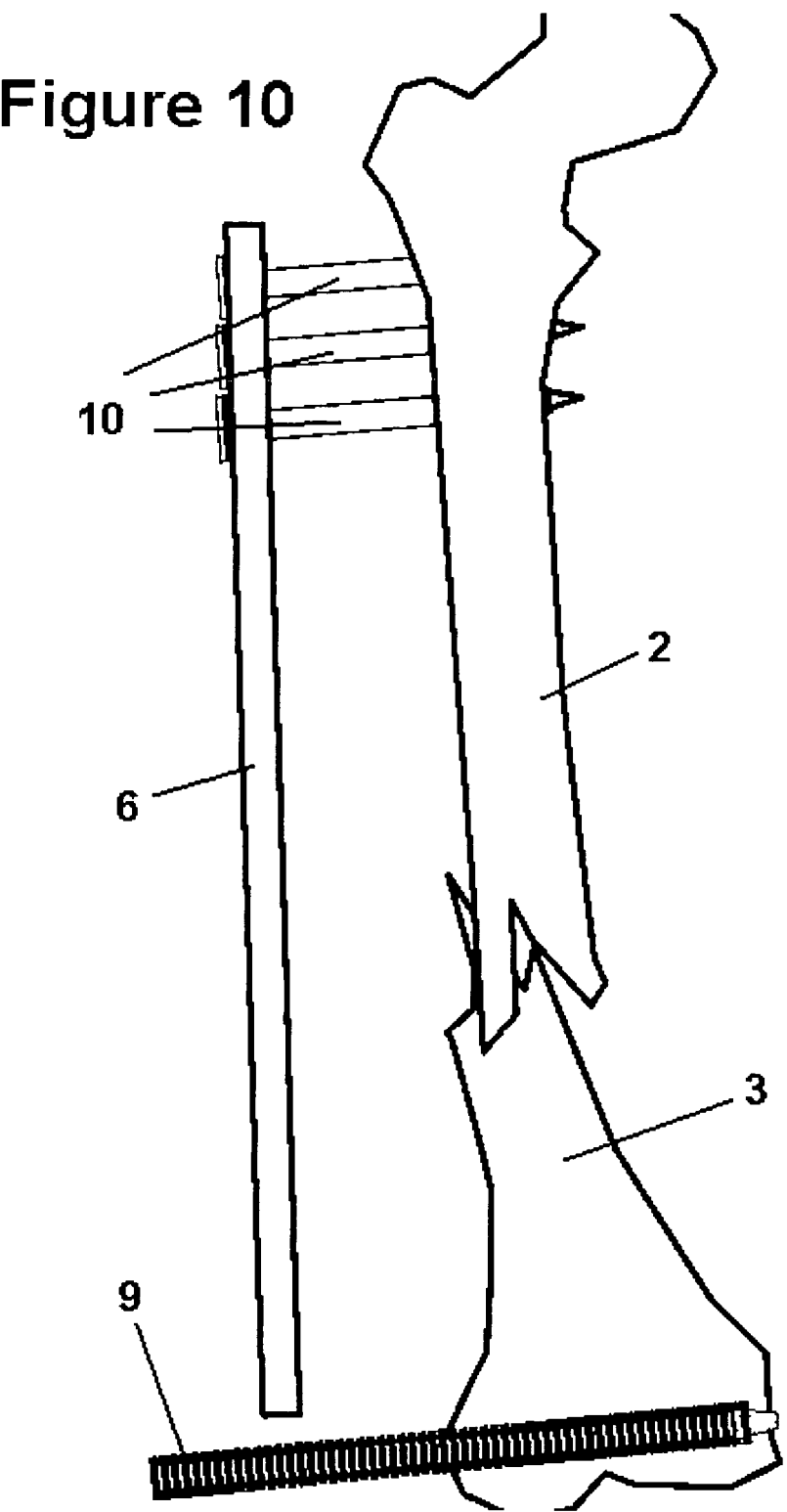
FIG. 10 depicts a method to manually distract the distal end of the bone using a threaded rod is inserted into the distal end.

Once one end of the bone (preferably the proximal end) is attached to the to subcutaneous elongated plate 6, the other portion of the bone (preferably the distal end) must be distracted and aligned to be attached to plate 6 and thereby fixed. The distraction may be performed manually by putting traction on the foot of the injured leg. Alternatively, the distraction can be performed manually as shown in FIG. 10. To manually distract the distal end of the bone 3, a threaded rod 9 is inserted into the distal end of the bone 3. This threaded rod 9 is used to manually pull the distal end of the bone into place.

In a preferred embodiment, the distraction is performed using a distraction device 20. The distraction device 20 is preferably attached to the plate 6 and the distal end of the bone 3 and allows the bone to be distracted and aligned so that the plate 6 can be attached to the distal end of the bone 3.

Figure 11:
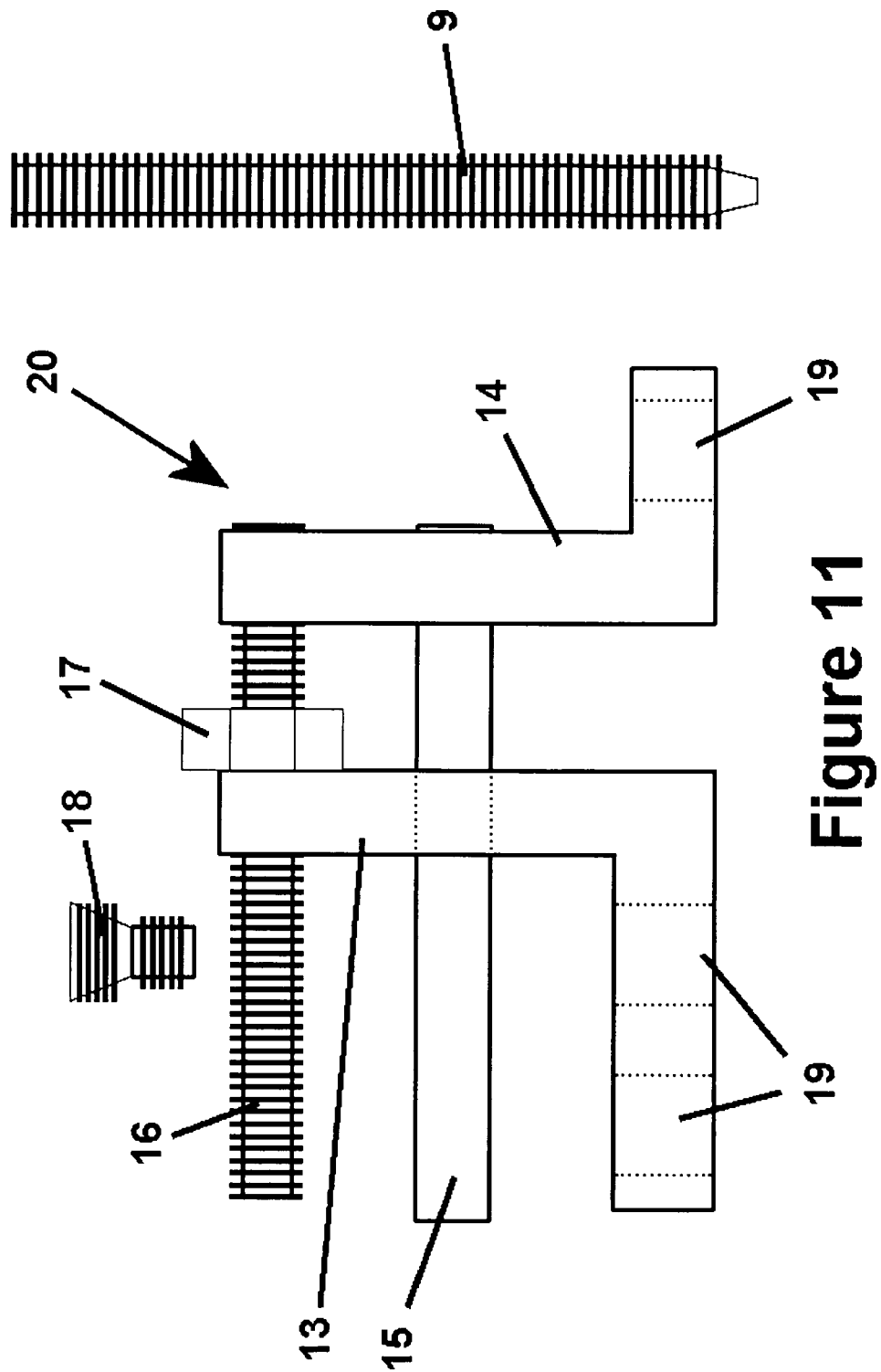
FIG. 11 depicts a preferred distraction device useful in conjunction with the method and device of the present invention.

FIG. 11 depicts a preferred distraction means 20. The distraction means 20 includes two distraction brackets 13 and 14. The distraction brackets 13 and 14 are three dimensional "L" shaped brackets. One of the brackets 13 has one or preferably two holes 19a on the horizontal leg of the "L" and two holes 21a and 21b on the vertical leg of the "L". Holes 19a are used in conjunction with locking screws or bolts 18 to affix bracket 13 to the elongated plate 6 as will be further discussed herein below. Holes 19a may be threaded or not, as needed. Holes 21a and 21b accommodate threaded rod 16 and smooth sliding rod 15, respectively, which rods are attached to bracket 14 as described below. Holes 21a and 21b are preferably not threaded and rods 15 and 16 readily slide through their respective holes.

Bracket 14 includes one hole 19b in the horizontal leg of the "L". Threaded rod 16 and smooth rod 15 are fixedly attached to the vertical leg of the "L" and extend horizontally out from the vertical leg of the "L" toward the through holes 21a and 21b of bracket 13. Hole 19b is used in conjunction with threaded rod 9 to attach bracket 14 to the distal portion of the bone 3. Finally, treaded rod 16 includes a distraction nut 17 threaded onto rod 16 and positioned between bracket 13 and bracket 14. The distraction nut 17 can push the two brackets 13 and 14 away from each other when the distraction nut 17 is turned the proper direction on the threaded rod 16.

Figure 13:
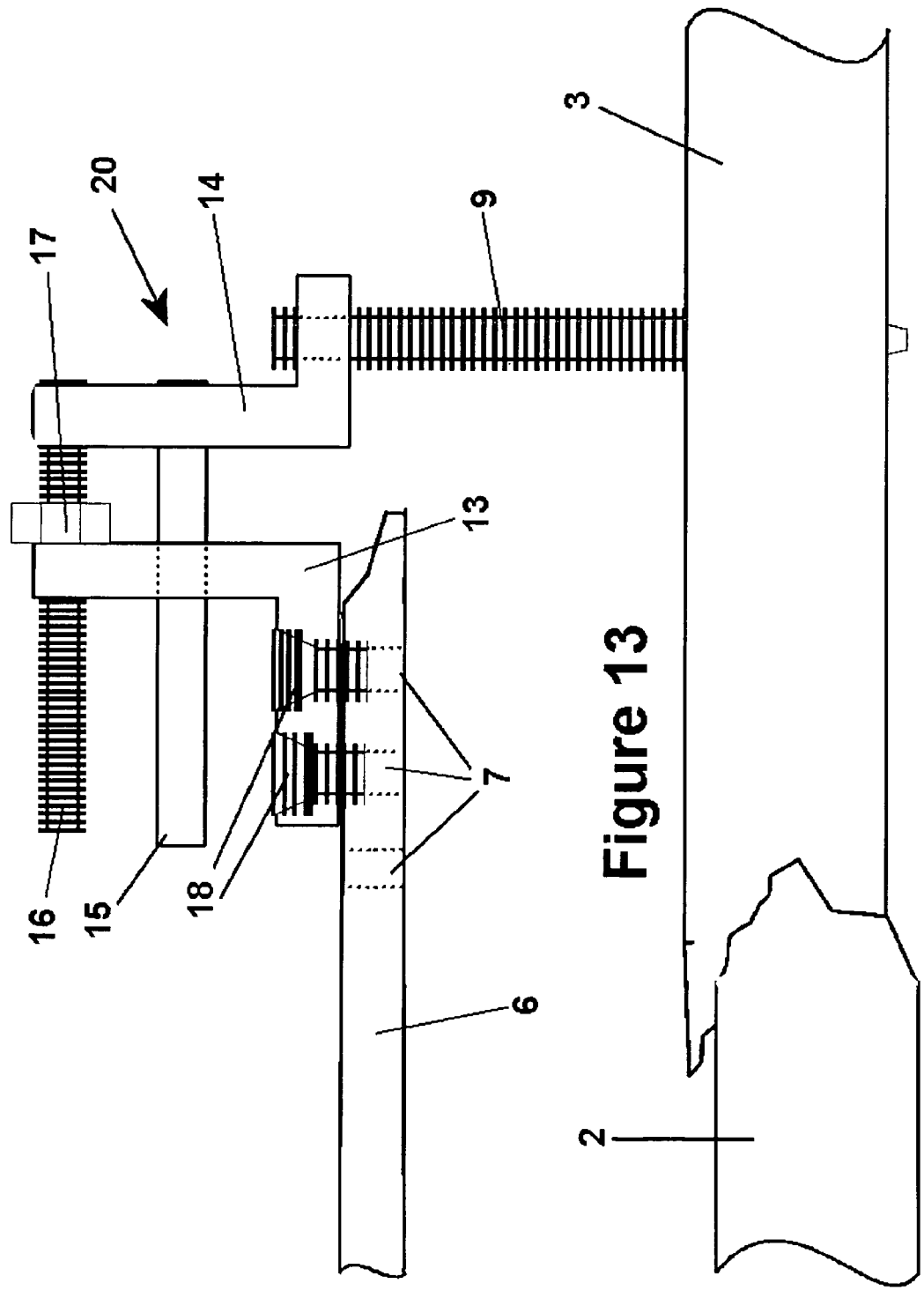
FIG. 13 depicts how the distraction device is attached to the plate using locking screws or bolts.
Figure 14:
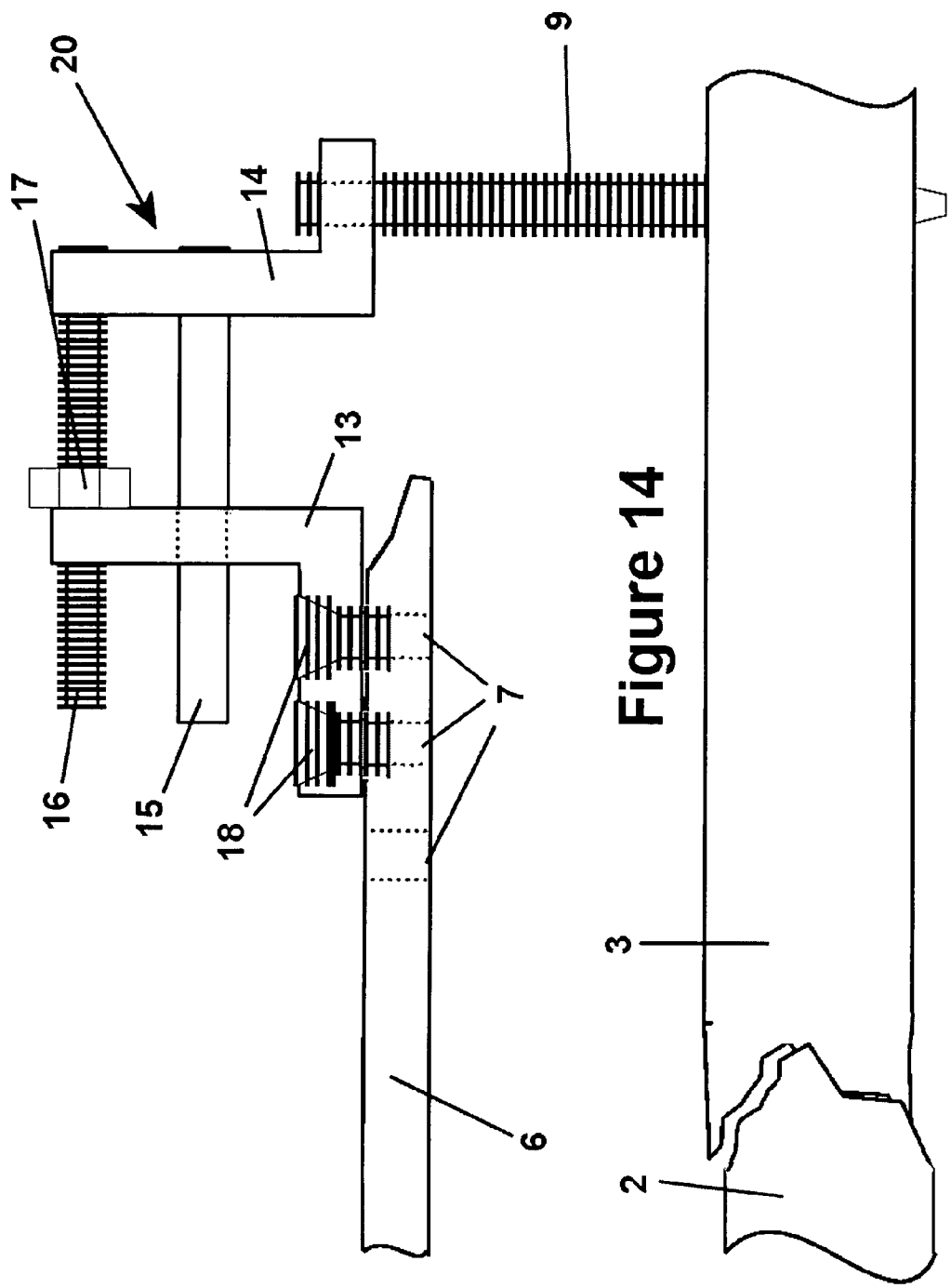
FIG. 14 shows that once the distraction device is attached to both the plate and distal end of the bone, the distraction nut is turned to expand distraction device by increasing the distance between the brackets.
Figure 15:
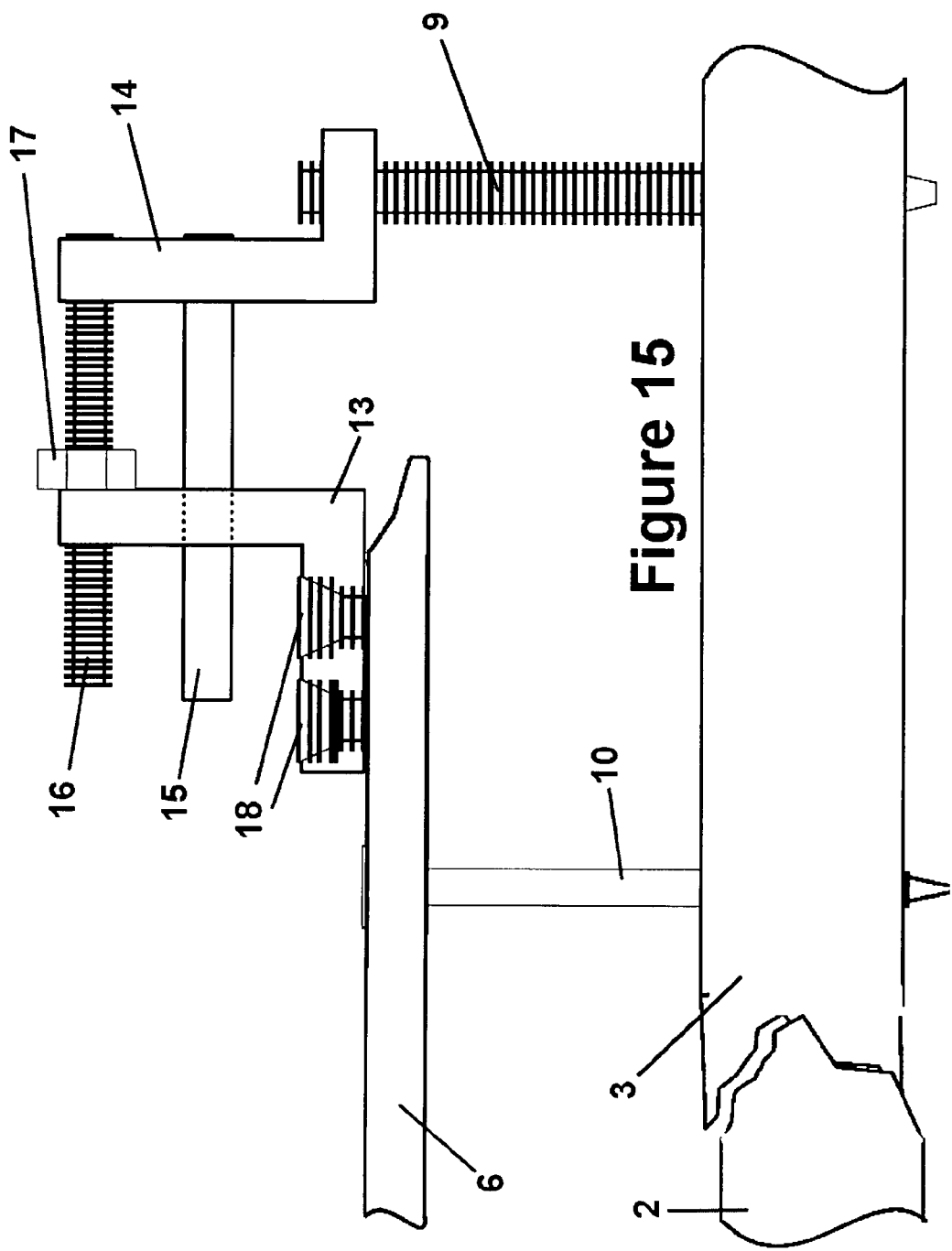
FIG. 15 shows that once the distal end of the bone is distracted and aligned, an attachment screw is inserted into the remaining hole on the plate and into the distal end of the bone.
Figure 16:
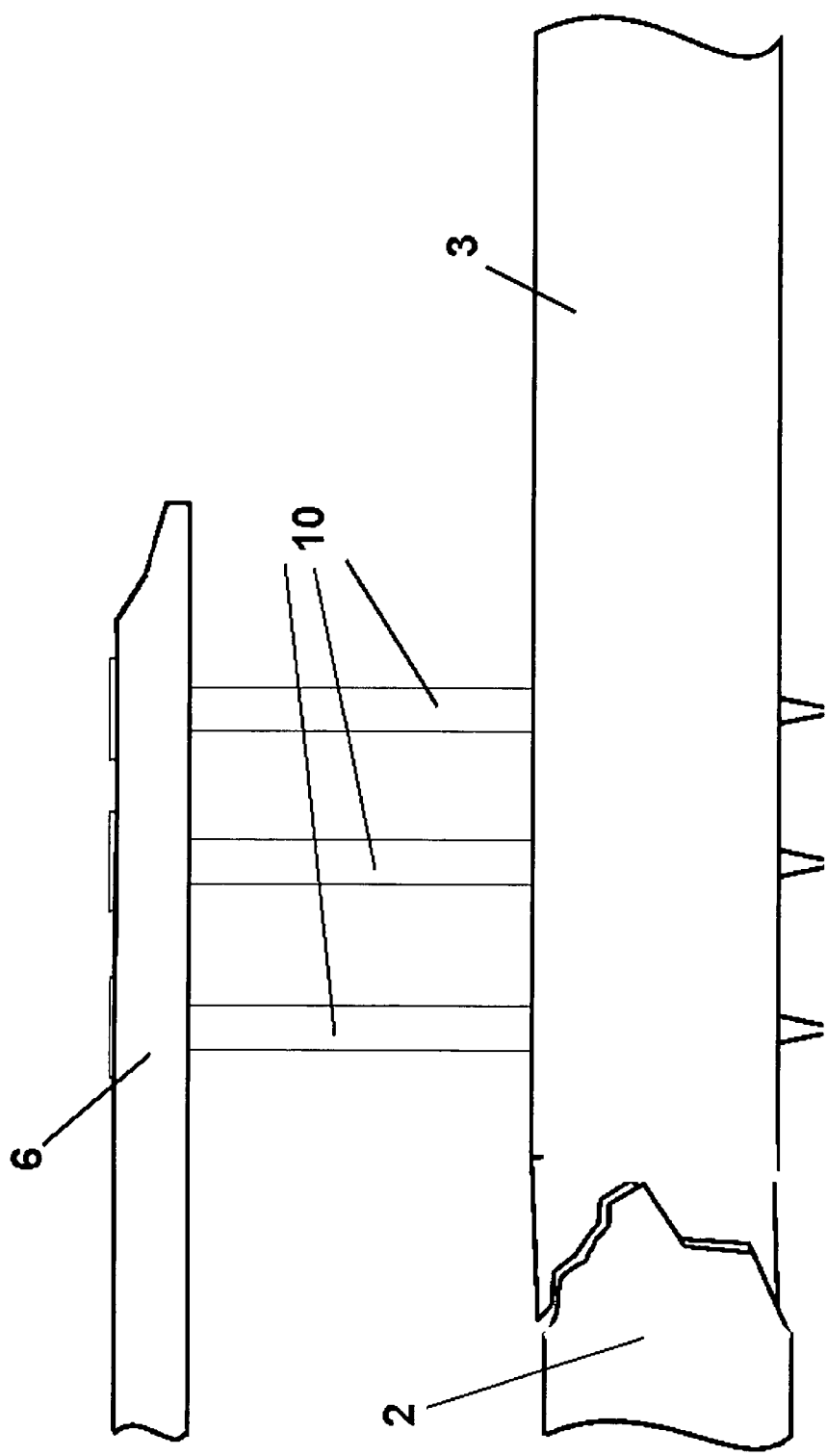
FIG. 16 depicts the removal of the distraction device, and the insertion of the remaining attachment screws through the other holes in the plate and into the distal end of the bone.
Figure 17:
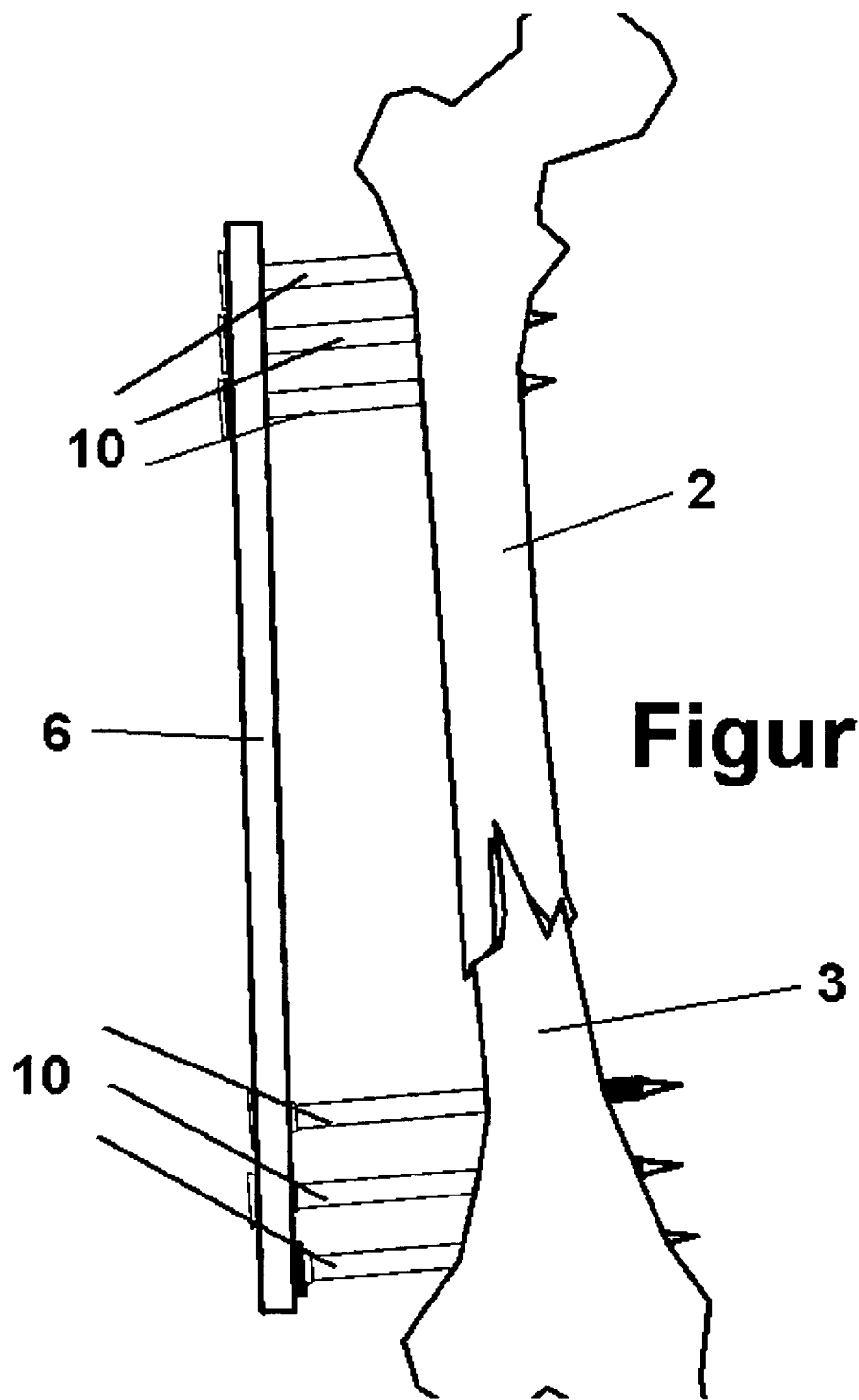
FIG. 17 shows the plate attached to both ends of the bone via attachment screws.

FIG. 12 shows how the distraction device 20 is aligned with plate 6. The holes 19a of bracket 13 are aligned with outermost holes 7 of the elongated plate 6. Once aligned, the distraction device is attached to plate 6 using locking screws or bolts 18 as shown in FIG. 13. The bolts 18 are threaded through holes 19a of bracket 13 and into holes 7 of elongated plate 6. After the distraction device 20 is attached to plate 6, a threaded rod is inserted through hole 19b in bracket 14 and into the distal end of the bone 3. Once the distraction device 20 is attached to both plate 6 and distal end of the bone 3, then the distraction nut 17 is turned to expand distraction device by increasing the distance between bracket 13 and 14 as shown in FIG. 14. Once the distal end of the bone 3 is distracted and aligned, an attachment screw 10 is inserted into the remaining hole 7 on plate 6 and into the distal end of the bone 3 as shown in FIG. 15. Once the first attachment screw 10 is in place in the distal end of the bone 3, distraction device 20 can be completely removed, and the remaining attachment screws 10 are inserted through the other holes in plate 6 and into the distal end of the bone 3 as shown in FIG. 16. FIG. 17 shows the plate attached to both ends of the bone 2, 3 via attachment screws 10.

Figure 18:
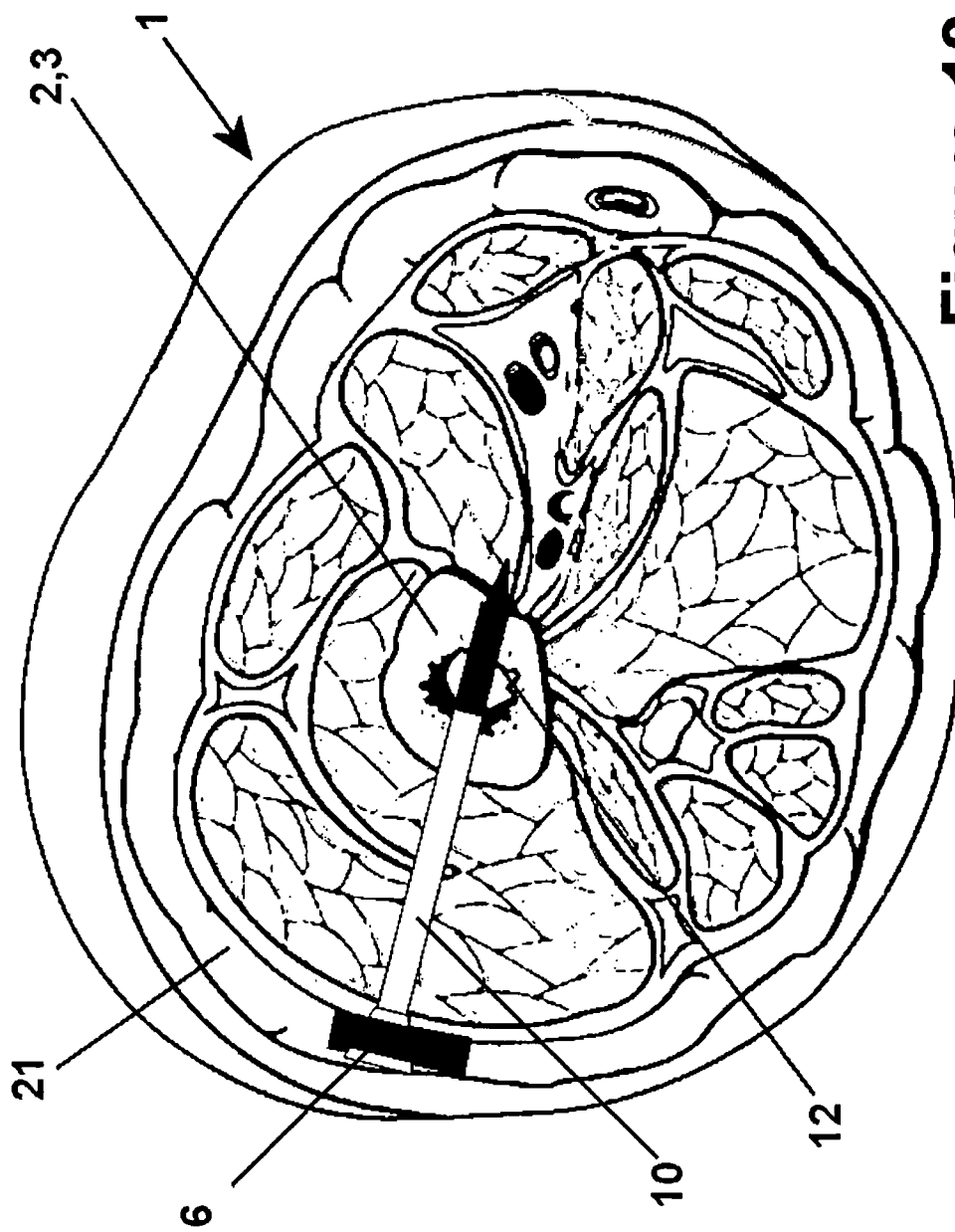
FIG. 18 is a depiction of a cross-section of a thigh having the elongated plate of the present invention disposed in the subcutaneous fat layer.

Finally, FIG. 18 is a depiction of a cross-section of a thigh 1 having the elongated plate 6 of the present invention disposed in the subcutaneous fat layer 22. The plate 6 is held to bone 2,3 using attachment screw 10, which has threads 12 only on the portion of the screw 10 that is in the bone.

Fixation of the Humerus

Figure 19:
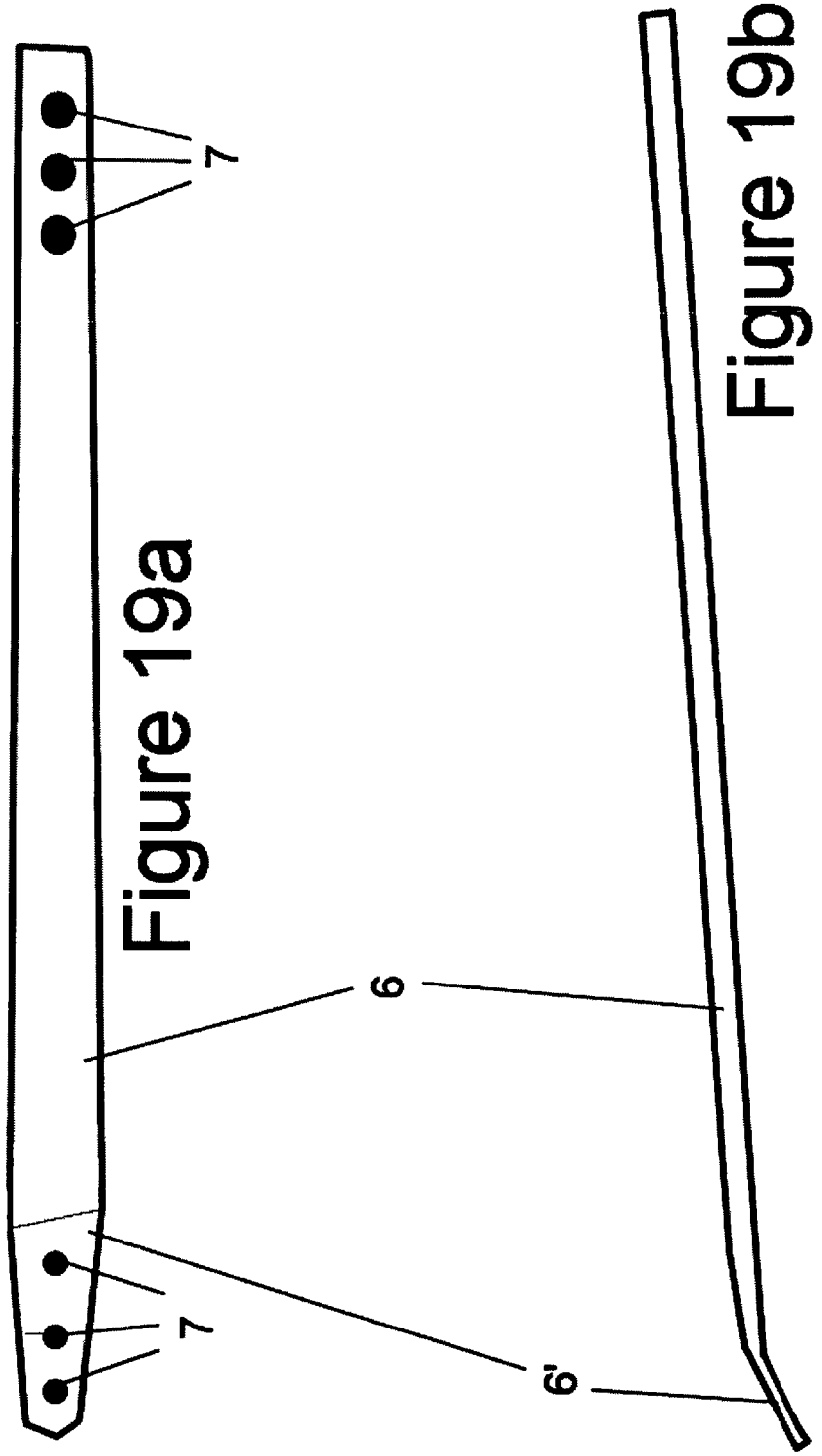
FIGS. 19a and 19b are schematic depictions of a top and side view, respectively, of an elongated plate useful in the present invention for use in fixation of a humerus fracture.

FIGS. 19a and 19b are schematic depictions of a top view and a side view of an elongated plate 6 useful in the fixation of a humerus by the method of the present invention. The plate 6 has at least two, and preferably three or more hole 7 in each end thereof. The holes 7 accommodate attachment means to attach the plate to the humerus. The holes 7 may be threaded as in locking plate technology. The holes 7 may also be non-threaded and the attachment means may include screws and nuts which can lock the plate near the end of the screws remote from the bone. It should be noted that elongated plate is based on locking plate technology but since it has significantly fewer holes, the device will cost less to produce. One end of the elongated plate 6 has an angled portion 6' designed to be affixed to the lateral epicondyle region in the distal end of the humerus.

Figure 20:
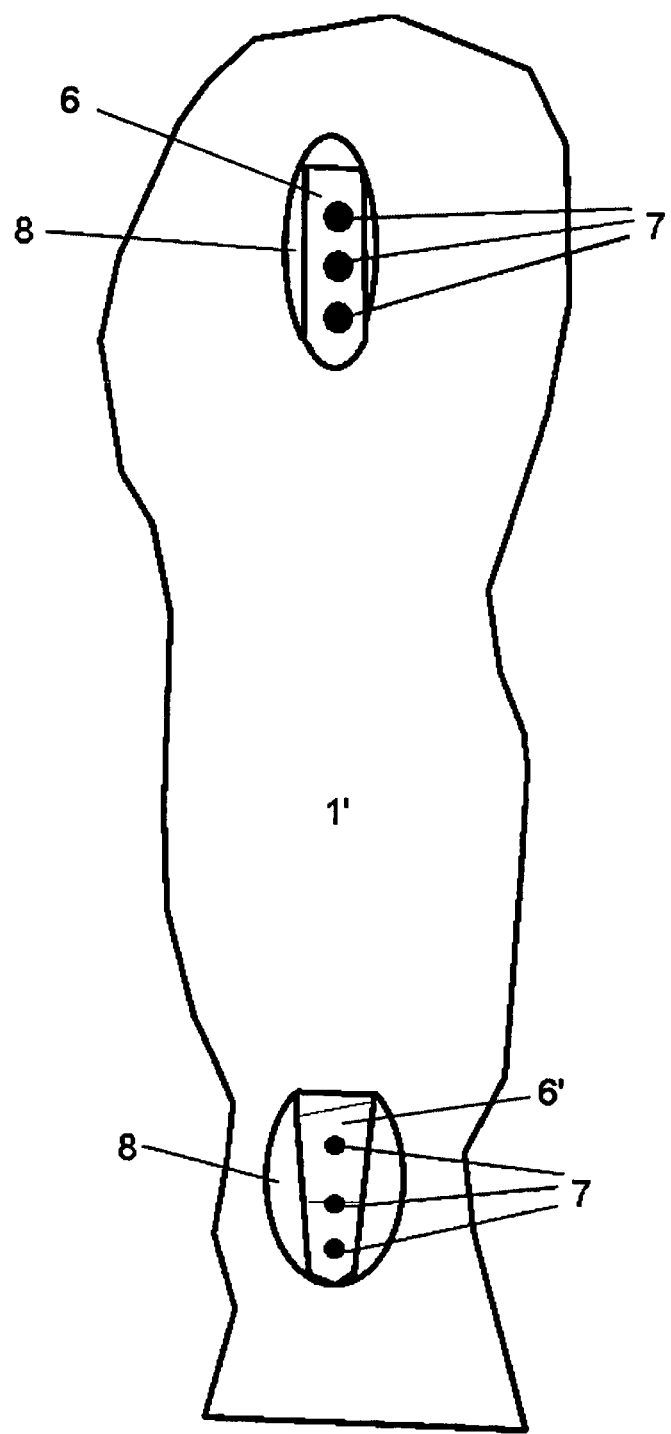
FIG. 20 is a schematic depiction of the manner in which the elongated plate may be placed subcutaneously in the brachium.
Figure 21:
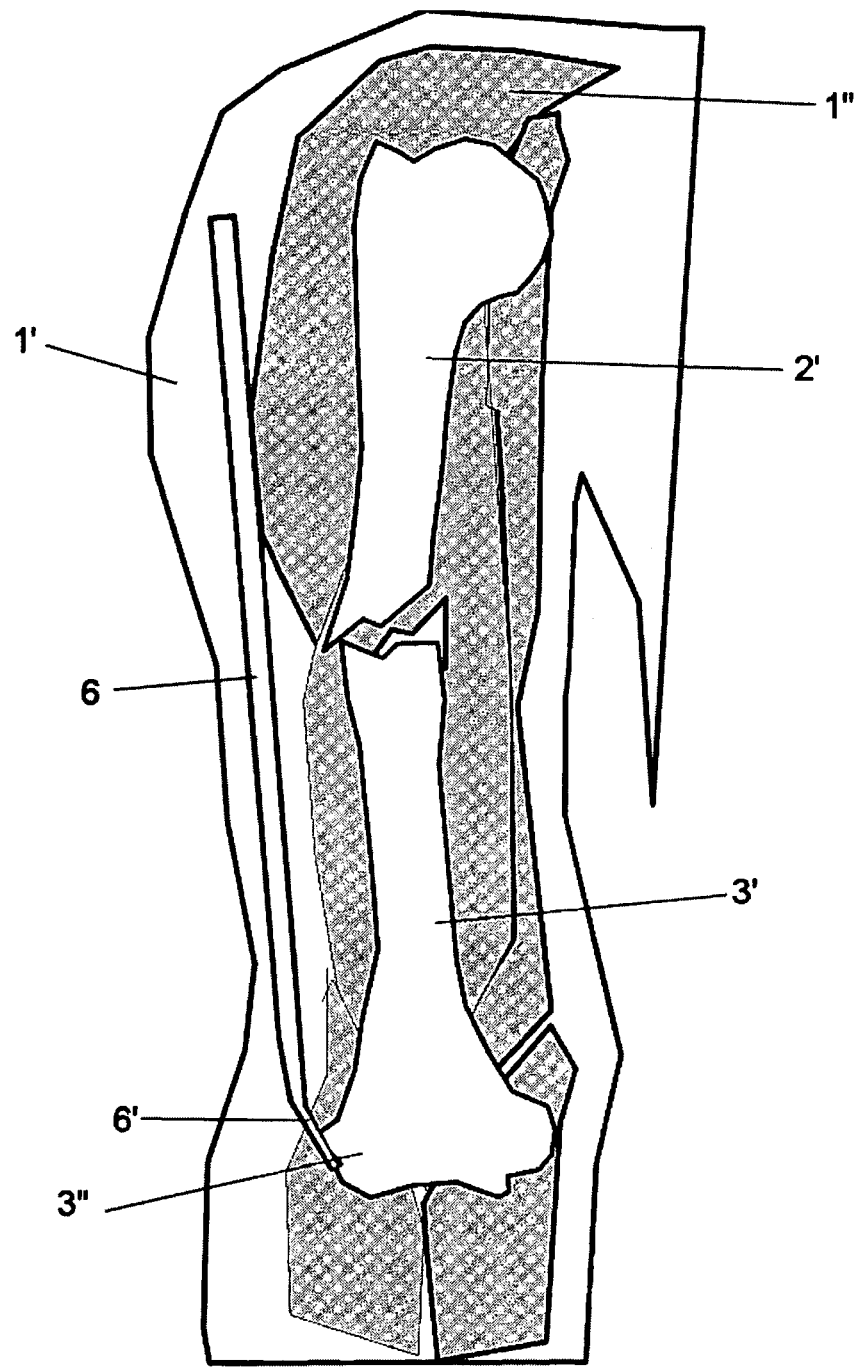
FIG. 21 is a schematic depiction of an alternative view of the manner in which the elongated plate is tunneled subcutaneously and supramuscularly inside the brachium and nearly parallel to the broken humerus between two incisions.

FIG. 20 is a schematic depiction of the manner in which the elongated plate 6 may be placed subcutaneously in the brachium 1'. The plate 6 may be placed into the subcutaneous fat layer through two incisions 8 in the skin. One incision is near the proximal end of the humerus and one is near the distal end of the humerus. The incisions 8 may be approximately 2 inches or less on each end and may preferably be placed in the lateral area of the brachium 1' when the bone being fixated 2',3' is a humerus. Of course, the plate 6 may come in many different sizes to accommodate different bone sizes. This placement of the elongated plate 6 just under the skin prevents disruption of the muscle tissue and since there is no dissection, there is little chance for infection. FIG. 5 is a schematic depiction of an alternative view of the manner in which the elongated plate 6 is tunneled subcutaneously and supramuscularly inside the brachium 1'. The elongated plate 6 runs essentially to the broken humerus 2',3' between the two incisions. The angled end 6' of the elongated plate 6 is place adjacent the lateral epicondyle region 3" of the distal end 3' of the humerus. Since there is little or no muscle 1" in this area of the brachium 1', the angled end 6' can at least partially contact the bone directly. The proximal end of the elongate plate 6 will be disposed above the muscles 1" of the brachium 1'.

Figure 22:
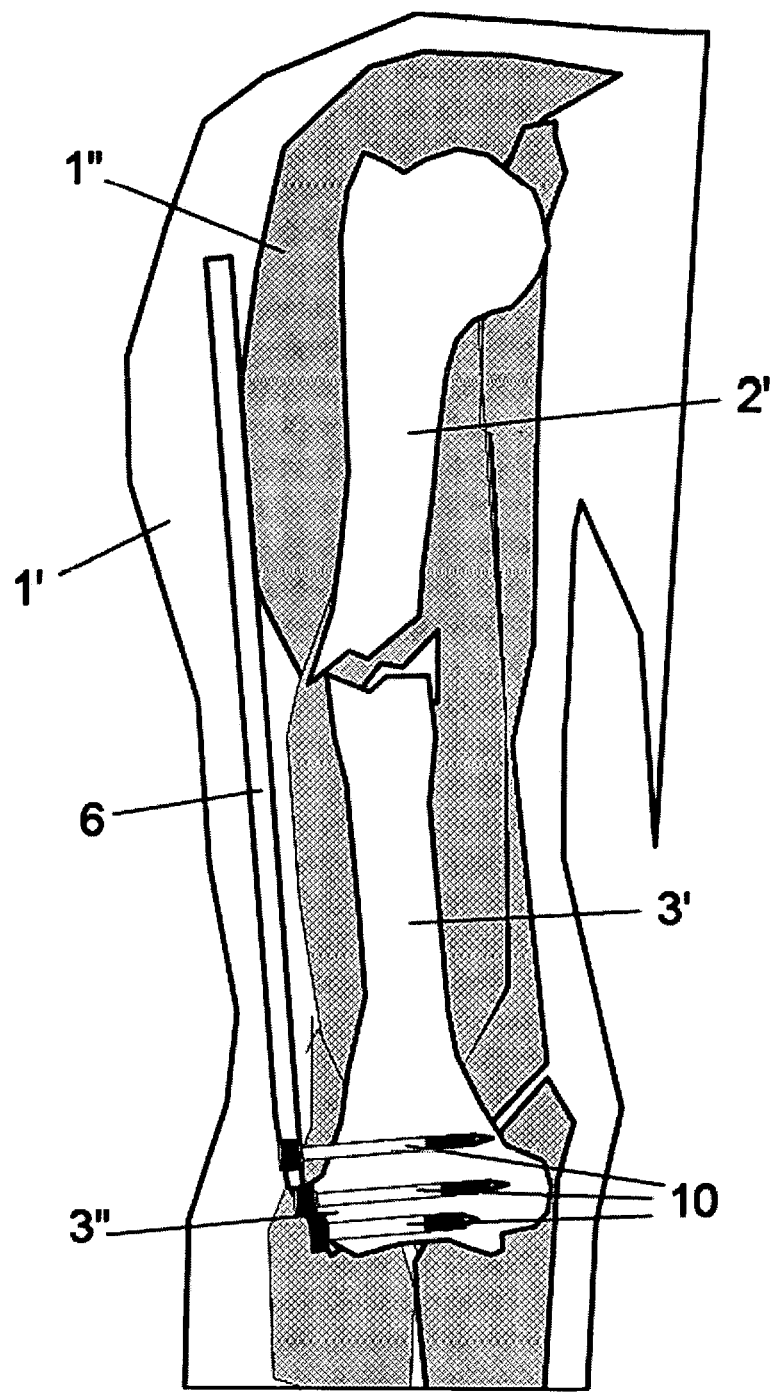
FIG. 22 is a schematic depiction of the manner in which three attachment screws 10 are inserted through holes in the angled end 6' of the elongated plate 6 and into the lateral epicondyle region 3" in the distal end 3' of the humerus.

As shown in FIG. 22, once the plate 6 has been placed into the brachium 1', attachment means 10 are inserted through the incision, through the holes in angled end 6' of the elongated plate 6 and into the distal end 3' of the humerus. As stated above, the plate 6 may have 2 or more holes in each end, preferably 3 or more. As with the femur example herein above, the threaded heads of the screws 10 may lock into the threaded holes of the plate 6 and the shaft of the screw 10 preferably only has thread only on the portion thereof which is inserted into the bone.

Figure 23:
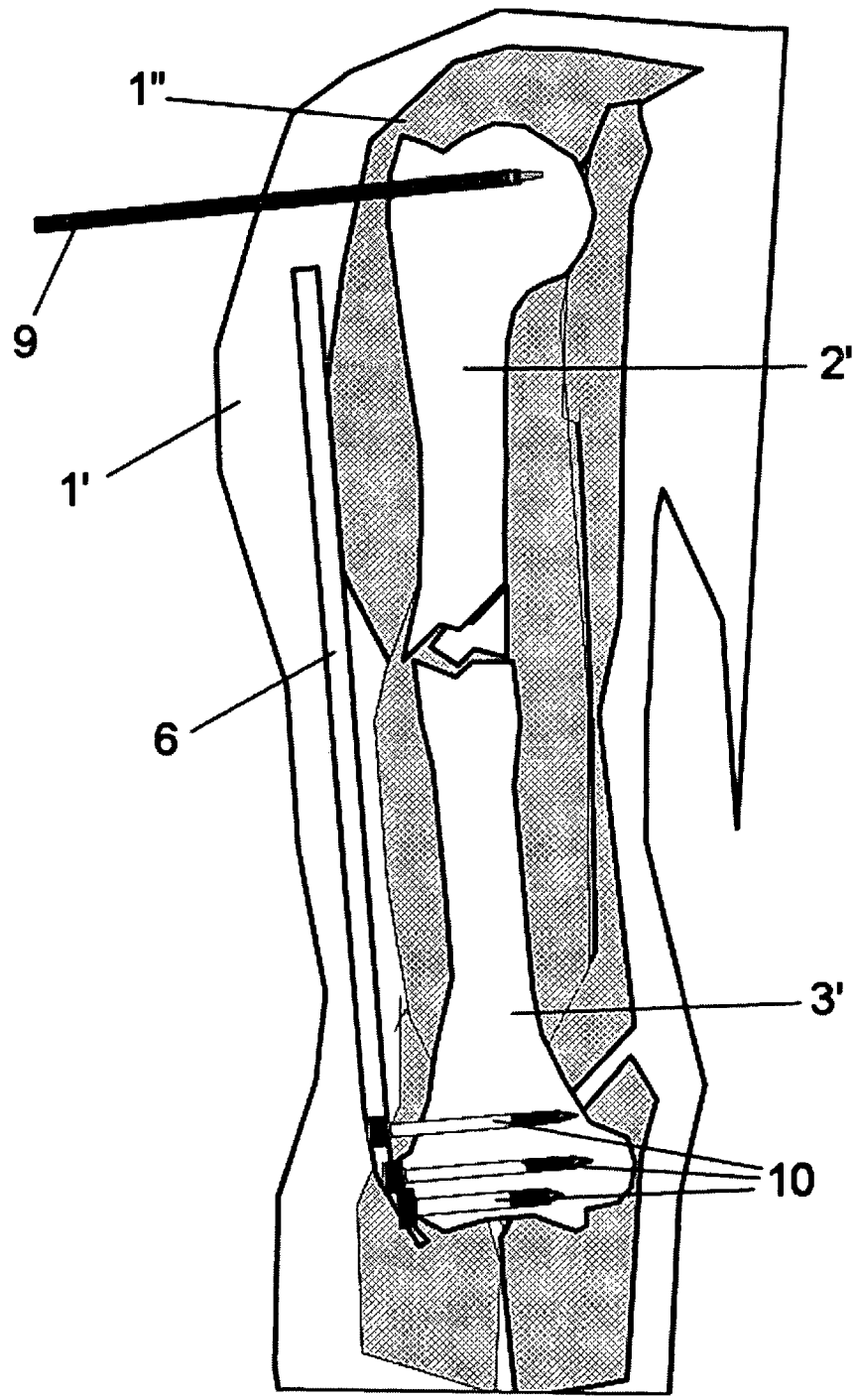
FIG. 23 depicts how a threaded rod 9 may be placed into the proximal end 2' of the humerus after the plate 6 has been placed into the brachium and attached to the distal end of the humerus 3', the rod being used to distract and align the proximal and distal ends of the humerus.

Once one end of the bone (preferably the distal end) is attached to the to subcutaneous elongated plate 6, the other portion of the bone (preferably the proximal end) must be distracted and aligned to be attached to plate 6 and thereby fixed. FIG. 23 depicts the manner in which the distraction may be performed manually by insertion of a threaded rod 9 into the proximal end 2' of the humerus. This threaded rod 9 is used to manually pull the proximal end of the humerus into place. Alternative, if desired the distraction device of FIG. 11 may be used in place of the manual distraction.

Figure 24:
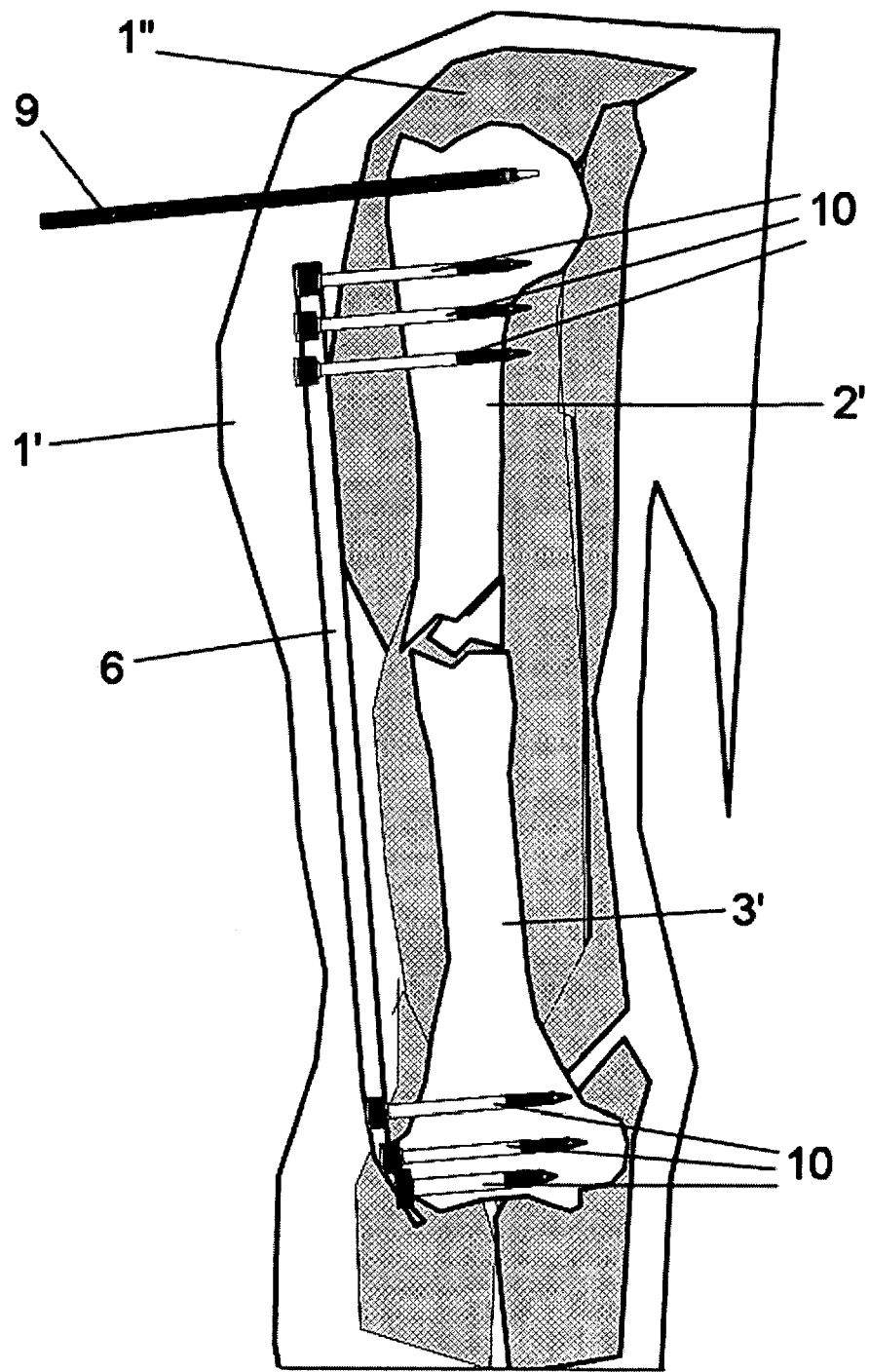
FIG. 24 depicts the insertion of the remaining attachment screws through the other holes in the proximal end of the plate and into the proximal end of the humerus.

Once the proximal end of the humerus 2' is distracted and aligned, attachment screws 10 are inserted into the remaining holes 7 on plate 6 and into the proximal end of the bone 2' as shown in FIG. 24, which depicts the elongated plate 6 attached to both ends of the humerus 2', 3' via attachment screws 10.

It is to be expected that considerable variations may be made in the embodiments disclosed herein without departing from the spirit and scope of this invention. Accordingly, the significant improvements offered by this invention are to be limited only by the scope of the following claims.

I claim:

1. A surgical method for minimally invasive treatment of humerus fractures comprising the steps of:
   tunneling an elongated plate subcutaneously and supramuscularly in the subcutaneous fat layer, the length dimension of said plate being generally substantially parallel to the length dimension of said fractured humerus; and
   attaching the ends of the elongated plate to the fractured humerus;
   wherein said elongated plate remains disposed in the subcutaneous fat layer and away from, but substantially parallel to the humerus once attached to the humerus.

2. The surgical method of claim 1, wherein said tunneling step includes creating one or more incisions in the skin through which said elongated plate can be inserted.

3. The surgical method of claim 2, wherein said one or more incisions in the skin are created on the lateral part of the brachium.

4. The surgical method of claim 1, wherein said step of attaching the ends of said elongated plate to said fractured humerus includes inserting attachment screws through holes in the ends of said elongated plate and into the humerus.

5. The surgical method of claim 4, wherein said holes in said elongated plate are threaded.

6. The surgical method of claim 5, wherein said attachment screws have threaded heads and said threaded heads allow said attachment screws to lock into said threaded holes of said elongated plate.

7. The surgical method of claim 4, wherein said step of attaching the ends of said elongated plate to said fractured humerus further includes the step of inserting said attachment screws through holes in an angled end of said elongated plate into the lateral epicondyle region of the distal end of said humerus.

8. The surgical method of claim 7, wherein said step of attaching the ends of said elongated plate to said fractured humerus further includes the step of inserting a threaded rod into the proximal end of said humerus said threaded rod being used to hold steady, distract and align said proximal end of said humerus before the step of inserting attachment screws through holes in the ends of said elongated plate and into the humerus.

9. The surgical method of claim 7, wherein said step of attaching the ends of said elongated plate to said fractured humerus further includes the step of distracting and aligning said fractured humerus.

10. The surgical method of claim 9, wherein said step of distracting and aligning said fractured humerus includes inserting a threaded rod into the proximal end of said humerus and manually distracting and aligning said fractured humerus.

11. The surgical method of claim 9, wherein said step of distracting and aligning said fractured humerus includes using a distraction device.

12. The surgical method of claim 11, wherein said step of using a distraction device includes the step of attaching said distraction device to said holes in the proximal end of said elongated plate and also attaching said distraction device to the proximal end of said humerus.

13. The surgical method of claim 12, wherein said distraction device has two brackets, where the first of said brackets is attached to said holes in the proximal end of said elongated plate and the second of said brackets is attached to the proximal end of said humerus.

14. The surgical method of claim 13, wherein said distraction device further includes an expansion device which is attached to both brackets and when used causes the brackets to expand away from each other thereby providing for distraction of said humerus.

15. The surgical method of claim 14, wherein said expansion device includes a threaded rod and a nut which is threaded onto said threaded rod, wherein said nut pushes against one of said brackets causing the brackets to expand away from each other thereby providing for distraction of said humerus.

16. The surgical method of claim 15, wherein said step of attaching the ends of said elongated plate to said fractured humerus further includes the step of inserting an attachment screw through a hole in a proximal end of said elongated plate into the proximal end of said humerus once said step of distracting and aligning said fractured humerus is completed.

17. The surgical method of claim 16, wherein said step of attaching the ends of said elongated plate to said fractured humerus further includes the step of removing said distraction device after said step of inserting an attachment screw through a hole in the proximal end of said elongated plate into the proximal end of said humerus.

18. The surgical method of claim 17, wherein said step of attaching the ends of said elongated plate to said fractured humerus further includes the step of inserting an additional attachment screw through each of the remaining holes in the proximal end of said elongated plate into the proximal end of said humerus.

19. The surgical method of claim 4, wherein said elongated plate and said attachment screws are formed from titanium, stainless steel or a bio-compatible polymer material.

* * * * *